(12) United States Patent
Myers, III et al.

(10) Patent No.: US 11,125,661 B2
(45) Date of Patent: Sep. 21, 2021

(54) DEVICES AND METHODS FOR BIOLOGICAL ASSAY SAMPLE PREPARATION AND DELIVERY

(71) Applicant: Lucira Health, Inc., Emeryville, CA (US)

(72) Inventors: Frank B. Myers, III, Richmond, CA (US); Wei Hsuan Ho, Foster City, CA (US); Debkishore Mitra, Berkeley, CA (US); John Robert Waldeisen, Berkeley, CA (US); Ivan Krastev Dimov, Union City, CA (US); Ryan C. Griswold, Los Gatos, CA (US); Bruce Richardson, Los Gatos, CA (US)

(73) Assignee: Lucira Health. Inc., Emeryville, CA (US)

( * ) Notice: Subject to any disclaimer, the term of this patent is extended or adjusted under 35 U.S.C. 154(b) by 374 days.

(21) Appl. No.: 16/081,799

(22) PCT Filed: Mar. 14, 2017

(86) PCT No.: PCT/US2017/022304
§ 371 (c)(1),
(2) Date: Aug. 31, 2018

(87) PCT Pub. No.: WO2017/160838
PCT Pub. Date: Sep. 21, 2017

(65) Prior Publication Data
US 2019/0094114 A1  Mar. 28, 2019

Related U.S. Application Data

(60) Provisional application No. 62/307,876, filed on Mar. 14, 2016.

(51) Int. Cl.
*G01N 1/30* (2006.01)
*G01N 1/38* (2006.01)
(Continued)

(52) U.S. Cl.
CPC .............. *G01N 1/30* (2013.01); *B01L 3/5029* (2013.01); *G01N 1/38* (2013.01);
(Continued)

(58) Field of Classification Search
CPC .... G01N 1/30; G01N 1/38; G01N 2001/4088; B01L 3/5029; B01L 2300/0672;
(Continued)

(56) References Cited

U.S. PATENT DOCUMENTS

| D244,555 S | 5/1977 | Wiedmann |
| 4,310,488 A | 1/1982 | Rahm et al. |

(Continued)

FOREIGN PATENT DOCUMENTS

| AU | 2003272465 A1 | 4/2004 |
| CA | 2495252 A1 | 3/2004 |

(Continued)

OTHER PUBLICATIONS

Anonymous: "Image Enhancement and Verification Tools—ABBYY Mobile Imaging SDK," Jul. 13, 2014, 12 pages.
(Continued)

*Primary Examiner* — Matthew D Krcha
*Assistant Examiner* — Jacqueline Brazin
(74) *Attorney, Agent, or Firm* — Goodwin Procter LLP

(57) ABSTRACT

Devices and methods for preparing and delivering biological assay samples are provided herein. Components of such devices include a sample receiving module within which a biological assay sample can be prepared and a cap, which when operatively coupled with the sample receiving module, pressurizes the module. These devices can be employed for subsequently delivering a biological assay sample.

22 Claims, 17 Drawing Sheets

(51) Int. Cl.
    *B01L 3/00*         (2006.01)
    *G01N 1/40*         (2006.01)
    *C12Q 1/6806*     (2018.01)

(52) U.S. Cl.
    CPC .................. *B01L 2300/0672* (2013.01); *B01L 2300/0681* (2013.01); *B01L 2300/0832* (2013.01); *B01L 2300/14* (2013.01); *B01L 2300/1877* (2013.01); *B01L 2400/0478* (2013.01); *B01L 2400/0487* (2013.01); *B01L 2400/0683* (2013.01); *C12Q 1/6806* (2013.01); *G01N 2001/4088* (2013.01)

(58) Field of Classification Search
    CPC ..... B01L 2300/0681; B01L 2300/0832; B01L 2300/14; B01L 2300/1877; B01L 2400/0478; B01L 2400/0487; B01L 2400/0683; C12Q 1/6806
    USPC ......................................................... 436/174
    See application file for complete search history.

(56)               References Cited

U.S. PATENT DOCUMENTS

| | | | |
|---|---|---|---|
| 4,379,848 | A | 4/1983 | Yeaw |
| 4,624,929 | A | 11/1986 | Ullman |
| 4,849,340 | A | 7/1989 | Oberhardt |
| 4,859,610 | A | 8/1989 | Maggio |
| 4,936,682 | A | 6/1990 | Hoyt |
| D334,065 | S | 3/1993 | Collister |
| D371,605 | S | 7/1996 | Wong et al. |
| 5,580,794 | A | 12/1996 | Allen |
| 5,801,062 | A * | 9/1998 | Sarstedt ............... B01L 3/0272 118/120 |
| 5,830,714 | A | 11/1998 | Swaminathan et al. |
| 5,837,546 | A | 11/1998 | Allen et al. |
| 5,888,826 | A | 3/1999 | Ostgaard et al. |
| 6,074,606 | A | 6/2000 | Sayles |
| 6,180,395 | B1 | 1/2001 | Skiffington et al. |
| 6,198,107 | B1 | 3/2001 | Seville |
| 6,336,900 | B1 | 1/2002 | Alleckson et al. |
| 6,352,838 | B1 | 3/2002 | Krulevitch et al. |
| 6,564,968 | B1 | 5/2003 | Terrell et al. |
| 6,565,808 | B2 | 5/2003 | Hudak et al. |
| 6,817,256 | B2 | 11/2004 | Mehra et al. |
| 6,900,059 | B1 | 5/2005 | Shinn et al. |
| D507,351 | S | 7/2005 | Birnboim |
| 7,156,809 | B2 | 1/2007 | Quy |
| D559,996 | S | 1/2008 | Okamoto et al. |
| D560,812 | S | 1/2008 | Powell et al. |
| D561,905 | S | 2/2008 | Ramel et al. |
| D574,507 | S | 8/2008 | Muir et al. |
| 7,438,852 | B2 | 10/2008 | Tung et al. |
| 7,452,667 | B2 | 11/2008 | Liew et al. |
| D608,885 | S | 1/2010 | Sneddon et al. |
| 7,850,922 | B2 | 12/2010 | Gallagher et al. |
| D659,848 | S | 5/2012 | TerMaat et al. |
| D669,375 | S | 10/2012 | Kao et al. |
| D686,311 | S | 7/2013 | Mori |
| D687,564 | S | 8/2013 | Yang et al. |
| 8,719,989 | B1 * | 5/2014 | Qanaei .................. B08B 9/0551 15/104.061 |
| 9,034,606 | B2 | 5/2015 | Tanner et al. |
| 9,074,243 | B2 | 7/2015 | Tanner et al. |
| 9,074,249 | B2 | 7/2015 | Tanner et al. |
| D743,571 | S | 11/2015 | Jackson |
| D748,813 | S | 2/2016 | Ishiguro et al. |
| D749,420 | S | 2/2016 | Maggio |
| 9,278,321 | B2 | 3/2016 | Dale et al. |
| D773,069 | S | 11/2016 | Curry |
| 9,546,358 | B2 | 1/2017 | Tanner et al. |
| D791,952 | S | 7/2017 | Florescu et al. |
| 9,739,743 | B2 | 8/2017 | Athanasiou et al. |
| D800,912 | S | 10/2017 | Uzri et al. |
| D808,833 | S | 1/2018 | Abbott et al. |
| D820,130 | S | 6/2018 | Khattak et al. |
| D821,602 | S | 6/2018 | Sever et al. |
| 9,999,889 | B2 | 6/2018 | Khattak et al. |
| D825,772 | S | 8/2018 | Sever et al. |
| 10,146,909 | B2 | 12/2018 | Dimov et al. |
| D838,379 | S | 1/2019 | Trump |
| 10,195,606 | B2 | 2/2019 | Khattak et al. |
| 10,253,357 | B2 | 4/2019 | Mitra et al. |
| 10,272,434 | B2 | 4/2019 | Khattak et al. |
| D855,212 | S | 7/2019 | Komuro |
| D859,683 | S | 9/2019 | Harding et al. |
| D860,472 | S | 9/2019 | Blake et al. |
| D865,212 | S | 10/2019 | Kakuda et al. |
| D867,584 | S | 11/2019 | Zercher et al. |
| D869,311 | S | 12/2019 | Khattak et al. |
| 10,545,161 | B2 | 1/2020 | Khattak et al. |
| 10,549,275 | B2 | 2/2020 | Myers, III et al. |
| D879,319 | S | 3/2020 | Kakuda et al. |
| D879,320 | S | 3/2020 | Kakuda et al. |
| 10,589,267 | B2 | 3/2020 | Khattak et al. |
| 10,603,664 | B2 | 3/2020 | Khattak et al. |
| 2002/0001539 | A1 * | 1/2002 | DiCesare ............... G01N 33/52 422/52 |
| 2002/0042125 | A1 | 4/2002 | Petersen et al. |
| 2003/0123994 | A1 | 7/2003 | Weng et al. |
| 2003/0157503 | A1 | 8/2003 | McGarry et al. |
| 2004/0018634 | A1 | 1/2004 | Hajizadeh et al. |
| 2004/0052689 | A1 | 3/2004 | Yao |
| 2004/0118189 | A1 | 6/2004 | Karp et al. |
| 2004/0166569 | A1 | 8/2004 | Marziali et al. |
| 2004/0209275 | A1 | 10/2004 | Liew et al. |
| 2005/0022895 | A1 | 2/2005 | Barth et al. |
| 2005/0221281 | A1 | 10/2005 | Ho |
| 2006/0078929 | A1 | 4/2006 | Bickel et al. |
| 2006/0094004 | A1 | 5/2006 | Nakajima et al. |
| 2006/0166354 | A1 | 7/2006 | Wikswo et al. |
| 2006/0194207 | A1 | 8/2006 | Mitani et al. |
| 2006/0245977 | A1 | 11/2006 | Bodner |
| 2007/0166200 | A1 | 7/2007 | Zhou et al. |
| 2007/0183934 | A1 | 8/2007 | Diercks et al. |
| 2007/0217963 | A1 | 9/2007 | Elizarov et al. |
| 2008/0000892 | A1 | 1/2008 | Hirano et al. |
| 2008/0038713 | A1 | 2/2008 | Gao et al. |
| 2008/0056948 | A1 | 3/2008 | Dale et al. |
| 2008/0149840 | A1 | 6/2008 | Handique et al. |
| 2008/0204380 | A1 | 8/2008 | Shin et al. |
| 2008/0233015 | A1 | 9/2008 | Turner |
| 2009/0004732 | A1 | 1/2009 | LaBarre et al. |
| 2009/0048115 | A1 | 2/2009 | Liew et al. |
| 2009/0071911 | A1 | 3/2009 | Folden et al. |
| 2009/0151864 | A1 | 6/2009 | Burke et al. |
| 2009/0203973 | A1 | 8/2009 | Donoghue et al. |
| 2009/0305315 | A1 | 12/2009 | Gandola et al. |
| 2009/0308185 | A1 | 12/2009 | Wu et al. |
| 2009/0320684 | A1 | 12/2009 | Weaver et al. |
| 2010/0015611 | A1 | 1/2010 | Webster et al. |
| 2010/0229956 | A1 | 9/2010 | Luyendijk |
| 2010/0331219 | A1 | 12/2010 | Munenaka |
| 2011/0003330 | A1 | 1/2011 | Durack |
| 2011/0124098 | A1 | 5/2011 | Rose et al. |
| 2011/0151432 | A1 | 6/2011 | Zappia et al. |
| 2011/0294112 | A1 | 12/2011 | Bearinger et al. |
| 2011/0294205 | A1 | 12/2011 | Hukari et al. |
| 2012/0100624 | A1 | 4/2012 | Hara et al. |
| 2012/0105837 | A1 | 5/2012 | Ingber |
| 2012/0285562 | A1 | 11/2012 | Richardson |
| 2013/0003162 | A1 | 1/2013 | Leoni et al. |
| 2013/0112296 | A1 | 5/2013 | Lee et al. |
| 2013/0130232 | A1 | 5/2013 | Weibel et al. |
| 2013/0244241 | A1 | 9/2013 | Fabra et al. |
| 2013/0266948 | A1 | 10/2013 | Bird et al. |
| 2013/0295663 | A1 | 11/2013 | Weight et al. |
| 2013/0323738 | A1 | 12/2013 | Tanner et al. |
| 2013/0323793 | A1 | 12/2013 | Tanner et al. |
| 2014/0031248 | A1 | 1/2014 | Tanner et al. |
| 2014/0057268 | A1 | 2/2014 | Tanner et al. |
| 2014/0073043 | A1 | 3/2014 | Holmes |
| 2014/0188089 | A1 | 7/2014 | Midgette et al. |

(56) References Cited

U.S. PATENT DOCUMENTS

| | | | |
|---|---|---|---|
| 2014/0228773 | A1 | 8/2014 | Burkholz |
| 2014/0242612 | A1 | 8/2014 | Wang et al. |
| 2014/0335505 | A1 | 11/2014 | Holmes |
| 2014/0356874 | A1 | 12/2014 | Bearinger |
| 2015/0024436 | A1 | 1/2015 | Eberhart et al. |
| 2015/0111201 | A1 | 4/2015 | Ozcan et al. |
| 2015/0132795 | A1 | 5/2015 | Griswold et al. |
| 2015/0151300 | A1 | 6/2015 | Williams et al. |
| 2015/0182966 | A1 | 7/2015 | Coursey |
| 2015/0240293 | A1 | 8/2015 | Tanner et al. |
| 2015/0247190 | A1 | 9/2015 | Ismagilov et al. |
| 2015/0298118 | A1 | 10/2015 | Chard et al. |
| 2015/0321193 | A1 | 11/2015 | Sprague et al. |
| 2015/0328638 | A1 | 11/2015 | Handique et al. |
| 2015/0359458 | A1 | 12/2015 | Erickson et al. |
| 2016/0077015 | A1 | 3/2016 | Holmes et al. |
| 2016/0194685 | A1 | 7/2016 | Unger et al. |
| 2016/0216287 | A1 | 7/2016 | Holmes et al. |
| 2016/0275149 | A1 | 9/2016 | Majumdar et al. |
| 2016/0334403 | A1 | 11/2016 | Gibbons et al. |
| 2017/0044599 | A1 | 2/2017 | Mitra et al. |
| 2018/0293350 | A1 | 10/2018 | Dimov et al. |
| 2019/0050988 | A1 | 2/2019 | Dimov et al. |
| 2019/0060895 | A1 | 2/2019 | Myers, III et al. |
| 2019/0076841 | A1 | 3/2019 | Myers, III et al. |
| 2019/0083975 | A1 | 3/2019 | Mitra et al. |
| 2019/0309356 | A1 | 10/2019 | Mitra et al. |
| 2019/0314810 | A1 | 10/2019 | Khattak et al. |
| 2020/0030798 | A1 | 1/2020 | Mitra et al. |
| 2020/0122142 | A1 | 4/2020 | Myers, III et al. |
| 2020/0164373 | A1 | 5/2020 | Khattak et al. |

FOREIGN PATENT DOCUMENTS

| | | | | |
|---|---|---|---|---|
| CN | 104937108 | A | 9/2015 | |
| CN | 105441312 | A | 3/2016 | |
| CN | 201930535293.7 | | 4/2020 | |
| EP | 0056241 | A1 | 7/1981 | |
| EP | 0520408 | A2 | 12/1992 | |
| EP | 1557673 | A1 | 7/2005 | |
| EP | 1661988 | A1 | 5/2006 | |
| EP | 2251435 | A1 | 11/2010 | |
| JP | 2008-173218 | A | 7/2008 | |
| JP | 2010-538801 | A | 12/2010 | |
| JP | 2013-526867 | A | 6/2013 | |
| JP | 2013-532488 | A | 8/2013 | |
| WO | 1997/012681 | A1 | 4/1997 | |
| WO | WO-9711723 | A1 * | 4/1997 | ............... A61L 2/26 |
| WO | 1997/041421 | A1 | 11/1997 | |
| WO | 2004/024892 | A2 | 3/2004 | |
| WO | 2005/012518 | A1 | 2/2005 | |
| WO | 2008/107014 | A1 | 9/2008 | |
| WO | 2009/033178 | A1 | 3/2009 | |
| WO | 2009/039259 | A1 | 3/2009 | |
| WO | WO-2009125227 | A1 * | 10/2009 | ........... G01N 33/581 |
| WO | 2010/091080 | A2 | 8/2010 | |
| WO | WO-2010132453 | A2 * | 11/2010 | ........... C12Q 1/6804 |
| WO | 2011/110873 | A1 | 9/2011 | |
| WO | 2011/123064 | A1 | 10/2011 | |
| WO | 2011/144345 | A1 | 11/2011 | |
| WO | 2012/018741 | A2 | 2/2012 | |
| WO | 2012/045889 | A1 | 4/2012 | |
| WO | 2013/008042 | A1 | 1/2013 | |
| WO | 2013/080154 | A1 | 6/2013 | |
| WO | 2014/018828 | A1 | 1/2014 | |
| WO | 2014/020326 | A2 | 2/2014 | |
| WO | 2014/031783 | A1 | 2/2014 | |
| WO | WO-2014019829 | A1 * | 2/2014 | ............. F28D 20/02 |
| WO | 2014/144548 | A2 | 9/2014 | |
| WO | 2015/164770 | A1 | 10/2015 | |
| WO | WO 2015/184360 | A1 | 12/2015 | |
| WO | 2017/160836 | A1 | 9/2017 | |
| WO | 2017/160838 | A1 | 9/2017 | |
| WO | 2017/160839 | A1 | 9/2017 | |
| WO | 2017/160840 | A1 | 9/2017 | |
| WO | 2018/140540 | A1 | 8/2018 | |
| WO | 2018/185573 | A1 | 10/2018 | |
| WO | 2019/055135 | A1 | 3/2019 | |

OTHER PUBLICATIONS

Canadian Office Action for Application No. 2,944,994, dated Aug. 8, 2019, 3 pages.

Cao et al., "Microfluidic Chip for Molecular Amplication of Influenza A RNA in Human Respiratory Specimens," PLoS One, Mar. 2012, vol. 7, Issue 3, pp. 1-11.

European Application No. 17767336.5, Extended European Search Report dated Sep. 26, 2019, 14 pages.

European Application No. 17767337.3, Extended European Search Report dated Sep. 18, 2019, 6 pages.

European Application No. 17767339.9, Extended European Search Report dated Oct. 4, 2019, 11 pages.

European Search Report for European Patent Application No. EP 19178796.9, dated Oct. 9, 2019, 7 Pages.

European Search Report, International Application No. EP18780624, dated Dec. 4, 2020, 10 pages.

Foo et al., "Rapid Tests for the Diagnosis of Influenza," Australian Prescriber, vol. 32, No. 3, Jun. 2009, pp. 64-67.

Goto., M., et al., "Colorimetric detection of loop-mediated isothermal amplification reaction by using hydroxy naphthol blue", Biotechniques, Mar. 1, 2009, pp. 167-172, vol. 46, No. 3.

Non-Final Office Action for U.S. Appl. No. 15/306,240, dated Jul. 24, 2018, 8 pages.

Non-Final Office Action for U.S. Appl. No. 16/359,913, dated Oct. 1, 2019, 9 pages.

Non-Final Office Action for U.S. Appl. No. 29/674,581, dated Jan. 8, 2020, 11 pages.

Partial Supplemental European Search Report for European Patent Application No. EP 17767338.1, dated Oct. 10, 2019, 15 Pages.

Patent Cooperation Treaty, International Search Report and Written Opinion of the International Searching Authority, International Patent Application No. PCT/US19/55365, dated Feb. 5, 2020, 20 Pages.

Patent Cooperation Treaty, International Search Report and Written Opinion of the International Searching Authority, International Patent Application No. PCT/US2015/027556, dated Sep. 15, 2015, 18 Pages.

Patent Cooperation Treaty, International Search Report and Written Opinion of the International Searching Authority, International Patent Application No. PCT/US2017/022300, dated Jul. 10, 2017, 15 Pages.

Patent Cooperation Treaty, International Search Report and Written Opinion of the International Searching Authority, International Patent Application No. PCT/US2017/022305, dated Jul. 19, 2017, 20 Pages.

Patent Cooperation Treaty, International Search Report and Written Opinion of the International Searching Authority, International Patent Application No. PCT/US2017/022306, dated Jun. 5, 2017, 18 Pages.

PCT International Search Report and Written Opinion for PCT/IB2018/051326, dated Jun. 26, 2018, 15 pages.

PCT International Search Report and Written Opinion for PCT/US2018/044044, dated Sep. 26, 2018, 13 Pages.

Supplementary European Search Report for European Patent Application No. EP 15783787, dated Nov. 28, 2017, 8 Pages.

Supplementary European Search Report for European Patent Application No. EP 17767338.1, dated Jan. 10, 2020, 13 Pages.

Westcott, S.L., et al., "Broadband optical absorbance spectroscopy using a whispering gallery mode microsphere resonator," Review of Scientific Instruments, vol. 79, No. 3, Mar. 13, 2008, 9 Pages.

Patent Cooperation Treaty, International Search Report and Written Opinion of the International Searching Authority, International Patent Application No. PCT/US2017/022304, dated Jul. 25, 2017, 20 Pages.

(56) References Cited

OTHER PUBLICATIONS

Extended European Search Report, European Published Application No. I 15557673 A1, dated May 25, 2021, 21 pages.

* cited by examiner

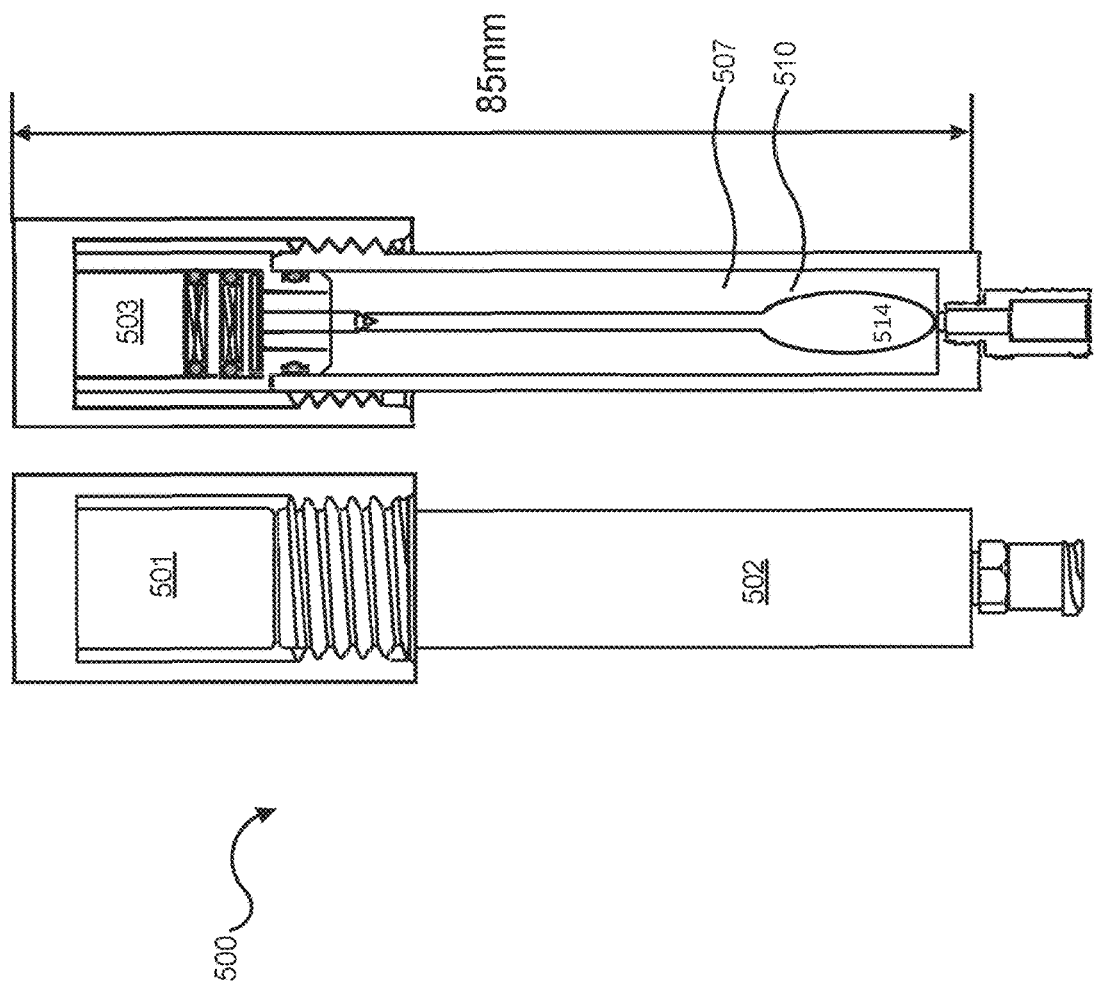

DEVICES AND METHODS FOR BIOLOGICAL ASSAY SAMPLE PREPARATION AND DELIVERY

RELATED APPLICATIONS

This application is a 35 U.S.C. 371 national stage filing of International Application No. PCT/US2017/022304, filed on Mar. 14, 2017, which claims priority from U.S. Provisional Patent Application No. 62/307,876 filed on Mar. 14, 2016, which are hereby incorporated by reference in their entireties.

INTRODUCTION

Biological assays sometimes require one or more fluids to be mixed, moved, separated and/or otherwise processed. Some biological assay devices and methods employ passive media control techniques such as capillary action for moving such fluids. Other methods and devices use active media control techniques which include propelling one or more fluids into, through and/or out of devices. Active media control techniques, in some instances, involve employing one or more pumps, such as electrically driven pumps, to create a fluid flow.

SUMMARY

Devices and methods for preparing and delivering biological assay samples are provided herein. Components of such devices include a sample receiving module within which a biological assay sample can be prepared and a cap, which when operatively coupled with the sample receiving module, pressurizes the module. These devices can be employed for subsequently delivering a biological assay sample.

Embodiments of the disclosed devices include a sample receiving module having a fluid container for receiving one or more portions of a sample collector therein, a preparation solution, such as a nucleic acid amplification preparation solution, and a first attachment element. Such devices can also include a cap, such as a cap which is removably coupleable to the sample receiving module and which includes a pressurizing component, and a second attachment element operatively coupleable with the first attachment element. In some versions of the devices, the pressurizing component extends into and pressurizes the sample receiving module for expelling fluid therefrom when the first attachment element is operatively coupled to the second attachment element. In some versions, the first attachment element is a thread and the second attachment element is a reciprocating groove for slidably receiving the thread therein. According to various aspects, the second attachment element extends concentrically around the pressurizing component.

In various aspects of the devices, a cap includes a receptacle configured to receive an end of the sample receiving module therein when the cap is coupled to the sample receiving module. The pressurizing component can extend from an interior surface of the cap and/or be disposed within the receptacle and/or can be integral with the cap. Also, in some aspects, the pressurizing component pressurizes the sample receiving module to a pressure ranging from 10 Pa to 30,000 Pa.

Where desired, the disclosed devices can be hand-held and/or can include a fluid container having a volume of 50 cm$^3$ or less. In some versions, the device includes a sample collector, such as a sample collector including a swab configured for collecting a biological sample.

In some embodiments, the pressurizing component is shaped substantially as a cylinder and/or the cap is shaped as a cylinder. In various embodiments, the sample receiving module is shaped as a cylinder having a diameter of 5 cm or less and having a height of 20 cm or less. Also, in some versions, the fluid container has a volume ranging from 1.0 cm$^3$ to 1.5 cm$^3$ and/or can contain from 1.0 cm$^3$ to 1.5 cm$^3$ of fluid therein.

In some instances, the sample receiving module includes a reversibly actuable valve configured to discharge fluid from the fluid container therethrough when actuated. In some aspects, the first attachment element is at a first end of the sample receiving module and the valve is at a second end of the sample receiving module opposite the first end. A device can also include one or more breakable seal, e.g., a seal including a foil sheet, for sealing the valve. A device can also include one or more re-sealable valve, e.g., a re-sealable puncture seal, e.g., a rubber septum, for sealing the valve. Such a valve may be incorporated in the device at the same location but instead of a breakable seal. A device can also include one or more filter for filtering fluid discharging through the valve. A filter can be configured to filter a sample fluid prior to discharging the sample fluid through the valve. As used herein the phrase "sample fluid" refers to fluid comprising sample that optionally can include any one or more reagents mixed with the sample within the sample preparation device.

Where appropriate, the sample receiving module includes an outer body forming a first chamber, and/or the fluid container includes a breakable seal and an inner body forming a second chamber, wherein the inner body is actuable within the outer body. In some versions, the outer body includes one or more piercing member. In some aspects, the inner body actuates within the outer body when the cap is coupled to the sample receiving module to break the seal with the piercing member and place the first and second chambers in fluidic communication. According to some aspects, the outer body and/or inner body includes a staging reagent, e.g., a lyophilized lysing reagent.

The subject devices also include biological assay sample preparation devices such as devices including a cap having a first chamber, a plunger including a piercing member, and a seal. Such devices can also include a sample receiving module, e.g., a sample receiving module configured to receive a biological sample collector therein, which is operatively coupleable to the cap and includes a second chamber. In some aspects, when the sample receiving module is operatively coupled to the cap, advancing the plunger pierces the seal with the piercing member and places the first chamber in fluidic communication with the second chamber.

As noted above, the subject disclosure is also drawn to methods of delivering a biological assay sample. The methods can include collecting a biological sample with a sample collector and/or inserting the sample collector into a sample receiving module of a sample preparation device. In some versions, inserting the sample collector includes exposing the biological sample to a preparation solution, e.g., a nucleic acid amplification preparation solution, to produce a prepared biological assay sample, e.g., a prepared nucleic acid amplification sample. The methods, in some aspects also include operatively coupling a cap of the sample preparation device to the sample receiving module and thereby pressurizing the sample receiving module. Additionally, where desired, the methods include delivering the prepared biological assay sample by depressurizing the sample receiving module by flowing at least a portion of the prepared biological assay sample out of the sample receiving module.

In some instances, a cap includes a pressurizing component and operatively coupling the cap involves inserting the pressurizing component into the sample receiving module. Pressurizing the sample receiving module can include pressurizing the module to a pressure ranging from 100 Pa to 30,000 Pa.

According to some aspects, operatively coupling a cap of the sample preparation device to the sample receiving module includes inserting an end of the sample receiving module into the cap. In some embodiments, operatively coupling a cap of the sample preparation device to the sample receiving module includes screwing the sample receiving module to the cap. In some embodiments, the sample receiving module and the cap are irreversibly engageable. For example, in some versions, when the cap is screwed back on, a user can screw it all the way down to a visually recognizable marker, e.g., a line, on the outside of the sample receiving module, at which point the cap will irreversibly engage by locking and will no longer re-open. Irreversibly engaging the components can also generate a clicking sound to notify a user of the irreversible engagement.

In some versions of the methods, the cap is operatively coupled to a first end of the sample preparation device and the sample receiving module includes a reversibly actuable valve at a second end of the sample preparation device opposite the first end. In some instances, the device further includes a breakable seal for sealing the valve and depressurizing the sample receiving module includes breaking the seal. In some versions, the methods also include filtering fluid discharging from the sample receiving module with a filter of a device.

According to various embodiments, the sample receiving module includes an outer body forming a first chamber, and wherein the fluid container includes a breakable seal and an inner body forming a second chamber, wherein the inner body is actuable within the outer body. In some aspects, operatively coupling a cap of the sample preparation device to the sample receiving module includes actuating the inner body within the outer body to break the seal and place the first and second chambers in fluidic communication. Also, where desired, the outer body includes a piercing member which breaks the seal when the inner body is actuated within the outer body. In addition, in some of the subject methods, the outer body and/or inner body includes a staging reagent and placing the first and second chambers in fluidic communication includes mixing the preparation solution and the staging reagent.

In some versions of the methods wherein the sample receiving module includes a first attachment element and the cap includes a second attachment element, operatively coupling a cap of the sample preparation device to the sample receiving module includes mateably connecting the first and second attachment elements. Also, in some aspects wherein the sample receiving module includes a breakable seal over an opening, inserting the sample collector into a sample receiving module of a sample preparation device includes breaking the seal and inserting at least a portion of the sample collector through the opening.

The subject methods also include methods of preparing one or more biological assay sample. Such methods can include operatively coupling a cap and a sample receiving module of a biological assay sample preparation device, wherein the cap includes a seal and a plunger including a piercing member. Such methods also, according to some embodiments, include advancing the plunger to pierce the seal with the piercing member and thereby placing the first chamber in fluidic communication with the second chamber and preparing the biological assay sample. Such methods can also include a step of inserting a biological sample collector into the sample receiving module.

Where desired, a plunger includes a first end and a second end opposite the first end and including the piercing member, and advancing the plunger includes exerting force on a first end of the plunger toward the second end. Also, in some versions, advancing the plunger includes screwing the cap to the sample receiving module.

In various embodiments, wherein the first chamber includes a preparation solution, the second chamber includes a staging reagent, placing the first chamber in fluidic communication with the second chamber mixes the preparation solution and the staging reagent. Also, in some versions, delivering the prepared biological assay sample includes actuating a reversibly actuable valve of the sample preparation device and flowing at least a portion of the prepared biological assay out of the sample receiving module through the valve.

BRIEF DESCRIPTION OF THE SEVERAL VIEWS OF THE DRAWINGS

FIG. 3A provides a partial cross sectional view of disclosed devices.

FIGS. 5A and 5B provide side views of devices according to embodiments of the subject disclosure. FIGS. 5A and 5B each includes a cross sectional view of disclosed devices.

DETAILED DESCRIPTION

Figure 1:
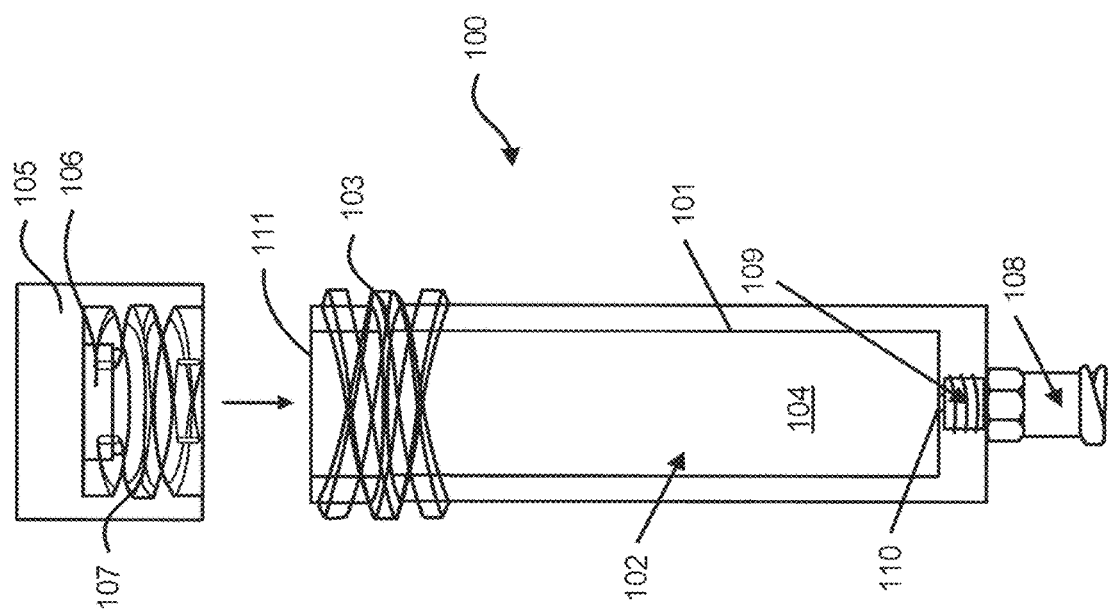
FIG. 1 provides a partial cross sectional view of a device according to embodiments of the subject disclosure.

Devices and methods for preparing and delivering biological assay samples are provided herein. Components of such devices include a sample receiving module within which a biological assay sample can be prepared and a cap, which when operatively coupled with the sample receiving module, pressurizes the module. These devices can be employed for subsequently delivering a biological assay sample.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided can be different from the actual publication dates which can need to be independently confirmed.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which can be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

In further describing the subject invention, subject devices for use in practicing the subject methods will be discussed in greater detail, followed by a review of associated methods.

Devices

Aspects of the subject disclosure include biological assay sample preparation devices.

As used herein, a "biological assay" is test on a biological sample which is performed to evaluate one or more characteristics of the sample. A biological sample is a sample containing a quantity of organic material, e.g., one or more organic molecules, such as one or more nucleic acids e.g., DNA and/or RNA or portions thereof, which can be taken from a subject. Accordingly, biological assay sample preparation devices, according to some embodiments, are devices which prepare a biological sample for analysis with a biological assay. Also, in some aspects a biological sample is a nucleic acid amplification sample, which is a sample including one or more nucleic acids or portions thereof which can be amplified according to the subject embodiments.

A biological sample can be collected from a subject and include one or more cells, such as tissue cells of the subject. As used herein, the term "tissue" refers to one or more aggregates of cells in a subject (e.g., a living organism, such as a mammal, such as a human) that have a similar function and structure or to a plurality of different types of such aggregates. Tissue can include, for example, organ tissue, muscle tissue (e.g., cardiac muscle; smooth muscle; and/or skeletal muscle), connective tissue, nervous tissue and/or epithelial tissue. Tissue can, in some versions, include cells from the inside of a subject's cheek and/or cells in a subject's saliva. A biological sample can also not include one or more cells. In some embodiments, a biological sample can include viral particles, free DNA, free RNA, bacteria cells or cell portions, fungi, spores, prions, or any combination thereof.

In some versions, and as described further below, a biological sample is collected from a subject. In certain embodiments, a subject is a "mammal" or a "mammalian"

subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" can include human subjects of both genders and at any stage of development (e.g., fetal, neonates, infant, juvenile, adolescent, and adult), where in certain embodiments the human subject is a juvenile, adolescent or adult. While the devices and methods described herein can be applied in association with a human subject, it is to be understood that the subject devices and methods can also be applied in association with other subjects, that is, on "non-human subjects."

One embodiment of a biological assay sample preparation device for use in practicing the subject methods is provided in FIG. 1. In various embodiments, the device 100 includes a sample receiving module 101 including a fluid container 102 for receiving one or more portions of a sample collector therein, e.g., entirely therein, a preparation solution 104, and a first attachment element 103. Such a device 100 can also include a cap 105 operatively, e.g., removably, coupleable to the sample receiving module 101 and including a pressurizing component 106, and a second attachment element 107 operatively coupleable with the first attachment element 103. In some embodiments of the devices, the pressurizing component 106 extends into and pressurizes the sample receiving module 101 for expelling fluid therefrom when the first attachment element 103 is operatively coupled to the second attachment element 107.

By "operatively coupled," "operatively connected" and "operatively attached" as used herein, is meant connected in a specific way that allows the disclosed devices to operate and/or methods to be carried out effectively in the manner described herein. For example, operatively coupling can include removably coupling or fixedly coupling two or more aspects. Operatively coupling can also include fluidically and/or electrically and/or mateably and/or adhesively coupling two or more components. Also, by "removably coupled," as used herein, is meant coupled, e.g., physically and/or fluidically and/or electrically coupled, in a manner wherein the two or more coupled components can be uncoupled and then re-coupled repeatedly.

Figure 15:
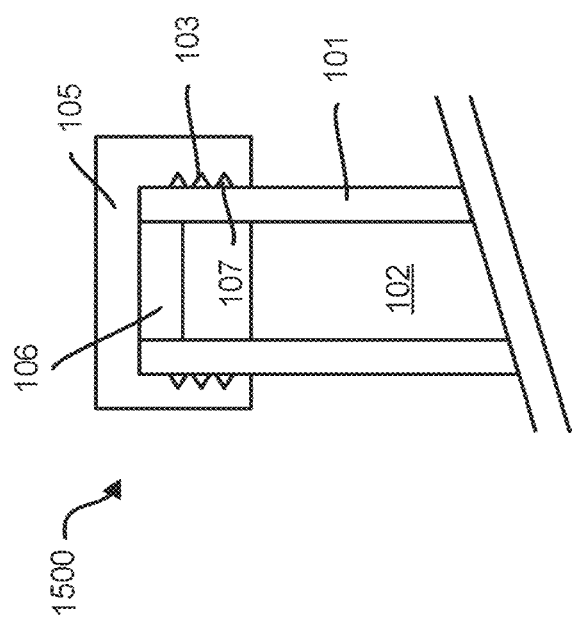
FIG. 15 provides a cross sectional view of a device according to embodiments of the present disclosure.

A portion of a biological assay sample preparation device for use in practicing the subject methods is provided in FIG. 15. The provided device 1500 portion includes many of the same elements of the embodiment shown in FIG. 1 including a cap 105 operatively, e.g., removably, coupled to the sample receiving module 101. Also provided is a fluid container 102, a first attachment element 103, and a second attachment element 107 operatively coupled with the first attachment element 103. As shown, the pressurizing component 106 extends into and pressurizes the sample receiving module 101 for expelling fluid therefrom when the first attachment element 103 is operatively coupled to the second attachment element 107.

Furthermore, and as is also shown in FIG. 1, the subject devices can also include one or more valve 108, e.g., a reversibly actuable valve. The devices can also include a variety of optional components, any one or combination of which can be included in the devices, including a filter 109 for filtering one or more fluids passing through a valve 108, a first seal 110, e.g., a breakable seal, for sealing an opening at an end of the sample receiving module 101 also including a valve 108, and/or a second seal 111, e.g., a breakable seal, for sealing an opening at an end of the sample receiving module 101 which is operatively coupleable with the cap 105.

As noted above, embodiments of the subject devices include a sample receiving module. Such a module can be configured to receive one or more portions of a biological sample described herein. Such a module can also be shaped, or shaped substantially, for example, as a cylinder and/or can be an elongated cylindrical tube. As used herein, "substantially" means to a great or significant extent, such as almost fully or almost entirely.

In embodiments wherein the sample receiving module is shaped as a cylinder, it can have a height, e.g., a height from one surface to an opposite surface, ranging from 1 cm to 50 cm, such as 1 cm to 10 cm, such as 1 cm to 5 cm, inclusive. The sample receiving module can also have a height of 50 cm or less, such as 30 cm or less, such as 20 cm or less, such as 10 cm or less, such as 5 cm or less, such as 3 cm or less, such as 1 cm or less. The sample receiving module can also have a height of 1 cm or more, such as 3 cm or more, such as 5 cm or more, such as 10 cm or more, such as 30 cm or more, such as 50 cm or more. Such a sample receiving module can also have a diameter, e.g., an outer diameter from an outer surface to an opposite outer surface, ranging from 1 mm to 5 cm, such as 1 mm to 3 cm, such as 1 mm to 1 cm, or 1 cm to 3 cm, each inclusive. Such a sample receiving module can also have a diameter, e.g., an outer diameter, of 5 cm or less, such as 3 cm or less, such as 1 cm or less, such as 5 mm or less, such as 3 mm or less, such as 1 mm or less. A sample receiving module can also have a diameter, e.g., an outer diameter, of 1 mm or more, such as 3 mm or more, such as 5 mm or more, such as 1 cm or more, such as 3 cm or more, such as 5 cm or more. A sample receiving module can also define an internal volume configured to receive any of the samples, and/or sample collectors, and/or preparation solutions described herein. Such an internal volume can range from, for example, 1 mm$^3$ to 500 cm$^3$, such as from 1 mm$^3$ to 200 cm$^3$, such as from 1 mm$^3$ to 100 cm$^3$, such as from 1 mm$^3$ to 10 cm$^3$, such as from 1 mm$^3$ to 5 cm$^3$, such as from 5 mm$^3$ to 1 cm$^3$, or from 1.5 cm$^3$ to 1 cm$^3$. A sample receiving module can also define an internal volume of 1 mm$^3$ or more, such as 1.5 cm$^3$ or more, such as 5 cm$^3$ or more, such as 1 cm$^3$ or more, such as 5 cm$^3$ or more, such as 10 cm$^3$ or more, such as 50 cm$^3$ or more, such as 100 cm$^3$ or more, such as 200 cm$^3$ or more, such as 300 cm$^3$ or more. A sample receiving module can also define an internal volume of 500 cm$^3$ or less, such as 300 cm$^3$ or less, such as 100 cm$^3$ or less, such as 50 cm$^3$ or less, such as 10 cm$^3$ or less, such as 5 cm$^3$ or less, such as 1.5 cm$^3$ or less, such as 1 cm$^3$ or less or 5 mm$^3$ or less.

A sample receiving module can have a first end, e.g., an open end having an opening which is sealable by a cap, and a second end, e.g., a closed end, opposite the first end. A first end can include a terminal flat surface which is insertable into, e.g., entirely insertable into, a cap. A pressurizing component can also be insertable into the first end of the sample receiving module. Furthermore, a second end, e.g., a closed end, can include one or more actuable valves, such as one or more reversibly actuable valves, such as reversibly actuable depressurization valves.

In some versions of the subject aspects, the devices include one or more valves, e.g., reversibly actuable depressurization valves. Such valves, can be configured to discharge fluid from a fluid container, e.g., a pressurized fluid container, therethrough when actuated. Valves according to the subject devices can be reversibly actuable between a first conformation and a second conformation. In the first conformation, the valve can provide an opening therethrough. Fluid, such as air and/or biological sample and/or a prepared sample and/or preparation solution, or any combination thereof, can pass through the opening in the valve when the valve is in the first conformation. In the second conformation, the valve is sealed and prevents the passage of fluid therethrough. The valve can be actuated from the first conformation to the second conformation by rotating the valve or a portion thereof, e.g., a first portion with respect to a second portion, such as by rotating the valve 45°, or 90° or 180° or 360° in a first rotational direction. The valve can be actuated from the second conformation to the first conformation by rotating the valve or a portion thereof, e.g., a first portion with respect to a second portion, such as by rotating the valve 45°, or 90° or 180° or 360° in a second rotational direction opposite the first rotational direction. In some versions, valves according to the subject embodiments are luer connectors, e.g., male and/or female luer connectors, and are mateably connectable to other luer connectors, e.g., male and/or female luer connectors. One or more valve according to the subject embodiments can be at an end of a sample receiving module opposite from an end attached to a cap when the sample receiving module is operatively coupled to the cap. In some versions, one or more valve according to the subject embodiments can be at an end of a sample receiving module opposite from an end at which an attachment element, e.g., a first attachment element, is positioned. Also, one or more valve according to the subject embodiments can be on a terminal flat surface of a sample receiving module and in some versions, can be centered on the surface. One or more valve according to the subject embodiments can also provide fluidic communication between a fluid container according to the subject embodiments and the environment external to the sample receiving module. The one or more valves can also include a locking element which provides tactile feedback to a user when the valve is operatively coupled to another and/or a sample preparation device is operatively coupled to an analyzing device.

In various embodiments, the sample receiving modules include a fluid container for containing one or more fluid, e.g., a liquid and/or a gas, and/or receiving one or more portions of a sample collector therein. Such a fluid container can be fluidically sealable such that, when sealed, fluids such as gasses and/or liquids cannot pass in or out of the container.

Sample receiving modules can include an outer surface and an interior surface defined by the one or more fluid container. Such a fluid container can extend inwardly from an opening, e.g., a circular opening, in a single flush and flat surface, e.g., a circular surface, of a sample receiving module at and end thereof. A fluid container can be configured to receive therein, e.g., entirely therein, one or more portions of a cap, e.g., a pressurizing component or an end thereof, when the cap is operatively coupled to the sample receiving module. A cap can also seal, e.g., fluidically seal, the fluid container of a sample receiving module when the cap is operatively coupled to the sample receiving module. A fluid container can be shaped as and/or define a cavity shape of a cylinder, rectangular box, pyramid, cube, or any combination thereof.

In embodiments where the fluid container is shaped as a cylinder, it can have a height ranging from 1 cm to 50 cm, such as 1 cm to 10 cm, such as 1 cm to 5 cm, inclusive. The fluid container can also have a height of 50 cm or less, such as 30 cm or less, such as 10 cm or less, such as 5 cm or less, such as 3 cm or less, such as 1 cm or less. The fluid container can also have a height of 1 cm or more, such as 3 cm or more, such as 5 cm or more, such as 10 cm or more, such as 30 cm or more, such as 50 cm or more. Such a fluid container can also have a diameter ranging from 1 mm to 5 cm, such as 1 mm to 3 cm, such as 1 mm to 1 cm, or 1 cm to 3 cm, each inclusive. Such a fluid container can also have a diameter of 5 cm or less, such as 3 cm or less, such as 1 cm or less, such as 5 mm or less, such as 3 mm or less, such as 1 mm or less. A fluid container can also have a diameter of 1 mm or more, such as 3 mm or more, such as 5 mm or more, such as 1 cm or more, such as 3 cm or more, such as 5 cm or more. A fluid container can also define an internal volume configured to receive any of the samples, and/or sample collectors, and/or preparation solutions described herein. Such an internal volume can range from, for example, 1 mm$^3$ to 500 cm$^3$, such as from 1 mm$^3$ to 200 cm$^3$, such as from 1 mm$^3$ to 100 cm$^3$, such as from 1 mm$^3$ to 10 cm$^3$, such as from 1 mm$^3$ to 5 cm$^3$, such as from 5 mm$^3$ to 1 cm$^3$, or from 1.5 cm$^3$ to 1 cm$^3$. A fluid container can also define an internal volume of 1 mm$^3$ or more, such as 5 mm$^3$ or more, such as 1 cm$^3$ or more, such as 1.5 cm$^3$ or more, such as 5 cm$^3$ or more, such as 10 cm$^3$ or more, such as 100 cm$^3$ or more, such as 200 cm$^3$ or more, such as 300 cm$^3$ or more. A fluid container can also define an internal volume of 500 cm$^3$ or less, such as 300 cm$^3$ or less, such as 100 cm$^3$ or less, such as 10 cm$^3$ or less, such as 5 cm$^3$ or less, such as 1.5 cm$^3$ or less, such as 1 cm$^3$ or less or 5 mm$^3$ or less.

Embodiments of the subject sample receiving modules include one or more attachment elements, e.g., first attachment elements. An attachment element can be configured to operatively couple the cap with a sample receiving module. Such an element can be disposed on an exterior surface, e.g., entirely on an exterior surface, of a sample receiving module or a portion thereof, e.g., a body of a sample receiving module. An attachment element can specifically include one or more engagement elements for mateably coupling with a cap or a portion thereof, e.g., an attachment element. In some versions, an attachment element of a sample receiving module can include a screwable thread and/or a thread track or groove, for screwing to a reciprocating thread or thread track or groove. In some versions, an attachment element, e.g., a first attachment element or a second attachment element, includes a thread and another, e.g., a second or a first, attachment element includes a reciprocating groove for slidably receiving the thread therein. Attachment elements according to the subject embodiments can also include one or more releasing element for releasing one attachment from another and which can include one or more button and/or lever and/or switch. Attachment elements, e.g., a first attachment element, can extend around, e.g., concentrically around, a pressurizing component of a device when a cap is operatively coupled with a sample receiving module. Attachment elements, e.g., a second attachment element, can also be exclusively outside, e.g., on an external surface of, or inside, e.g., on an internal surface of, a sample receiving module or a portion thereof, e.g., a body. In other words, all portions of an attachment element can fall between at least two other portions of the sample receiving module, e.g., sample receiving module body.

As noted above, in some aspects of the subject disclosure, the devices include a preparation solution. In some versions of the subject disclosure, the preparation solution is a nucleic acid amplification preparation solution and can include one or more buffer. A nucleic acid amplification preparation solution is a solution which prepares a biological sample such that one or more nucleic acid thereof can be amplified, e.g., amplified isothermally.

Also, the phrases "nucleic acid amplification" or "amplification reaction" refers to methods of amplifying DNA, RNA, or modified versions thereof. Nucleic acid amplification includes several techniques, such as an isothermal reaction or a thermocycled reaction. More specifically, nucleic acid amplification includes methods such as polymerase chain reaction (PCR), loop-mediated isothermal amplification (LAMP), strand displacement amplification (SDA), recombinase polymerase amplification (RPA), helicase dependent amplification (HDA), multiple displacement amplification (MDA), rolling circle amplification (RCA), and nucleic acid sequence-based amplification (NASBA). The phrase "isothermal amplification" refers to an amplification method that is performed without changing the temperature of the amplification reaction. Protons are released during an amplification reaction: for every deoxynucleotide triphosphate (dNTP) that is added to a single-stranded DNA template during an amplification reaction, one proton ($H^+$) is released.

A nucleic acid amplification preparation solution can be a solution that prepares a biological sample for amplification with an isothermal amplification protocol including: transcription mediated amplification, strand displacement amplification, nucleic acid sequence-based amplification, rolling circle amplification, loop-mediated isothermal amplification, isothermal multiple displacement amplification, helicase-dependent amplification, circular helicase-dependent amplification, single primer isothermal amplification, loop-mediated amplification, or any combination thereof.

In various embodiments, a preparation solution, such as a nucleic acid amplification preparation solution, includes one or more lysing agent, such as one or more detergent. Such a lysing agent can, for example, include dithiothreitol (DTT), detergents, e.g., TRITON X-100™, TWEEN®, Sodium dodecyl sulfate (SDS), dichlorodiphenyltrichloroethane (DDT), chaotropic salts, acids and/or bases, pH buffers, beads, solvents, or any combinations thereof. Such an agent can lyse cells of a biological sample to release nucleic acids therefrom. A preparation solution, such as a nucleic acid amplification preparation solution, can also include $H_2O$ and/or one or more buffer.

In some versions of the subject disclosure, the devices include one or more sample collector. A sample collector can be configured for obtaining and/or retaining a biological sample as described herein. A sample collector can also be configured for fitting into and/or being retain within, e.g., entirely within, a sample receiving module, such as a sample receiving module operatively coupled to a cap. A sample collector can be retained within, e.g., entirely within, a sample receiving module, such as a sample receiving module operatively coupled to a cap while preparing a sample and/or delivering a prepared sample as described herein.

Embodiments of the subject sample collectors can extend longitudinally from a handle to a sample collection element at an end opposite the handle. A sample collector can be or include a swab, such as a cotton swab, configured for collecting and/or retaining a biological sample. Sample collectors can also be or include a scraping element for scraping a biological sample source to obtain the biological sample. A sample collector can also be or include a container, such as a sealable container for retaining a biological sample. Sample collectors according to the subject embodiments also can include one or more syringe, hollow capillary tube, punch tool, or any combination thereof.

A sample collector can be substantially shaped, for example, as a cylinder or a rectangular box. In embodiments where the sample collector is shaped as a cylinder, it can have a height ranging from 1 cm to 50 cm, such as 1 cm to 20 cm, such as 1 cm to 10 cm, such as 1 cm to 5 cm, such as from 1 cm to 3 cm inclusive. The sample collector can also have a height of 50 cm or less, such as 30 cm or less, such as 20 cm or less, such as 10 cm or less, such as 5 cm or less, such as 3 cm or less, such as 1 cm or less. The sample collector can also have a height of 1 cm or more, such as 3 cm or more, such as 5 cm or more, such as 10 cm or more, such as 20 cm or more, such as 30 cm or more, such as 50 cm or more. Such a sample collector can also have a diameter ranging from 1 mm to 5 cm, such as 1 mm to 3 cm, such as 1 mm to 1 cm, or 1 cm to 3 cm, each inclusive. Such a sample collector can also have a diameter of 5 cm or less, such as 3 cm or less, such as 1 cm or less, such as 5 mm or less, such as 3 mm or less, such as 1 mm or less. A sample collector can also have a diameter of 1 mm or more, such as 3 mm or more, such as 5 mm or more, such as 1 cm or more, such as 3 cm or more, such as 5 cm or more. Sample collectors can also have or define a total volume ranging from, for example, 1 $mm^3$ to 200 $cm^3$, such as from 1 $mm^3$ to 100 $cm^3$, such as from 1 $mm^3$ to 10 $cm^3$, such as from 1 $mm^3$ to 5 $cm^3$, such as from 5 $mm^3$ to 1 $cm^3$. A sample collector can also have a volume of 1 $mm^3$ or more, such as 5 $mm^3$ or more, such as 1 $cm^3$ or more, such as 5 $cm^3$ or more, such as 10 $cm^3$ or more, such as 100 $cm^3$ or more, such as 200 $cm^3$ or more. Sample collectors can also have a volume of 200 $cm^3$ or less, such as 100 $cm^3$ or less, such as 10 $cm^3$ or less, such as 5 $cm^3$ or less, such as 1 $cm^3$ or less or 5 $mm^3$ or less.

As noted above, embodiments of the subject devices include a cap. Such a cap can be configured to operatively couple, e.g., reversibly couple and/or sealably couple, to a sample receiving module. Accordingly, such a cap can be configured for sealing one or more opening of a sample receiving module. A cap can have a first end, e.g., an open end having an opening which defines a receptacle, and a second end, e.g., a closed and/or sealed end, opposite the first end and defined by a single flat terminal surface.

In various embodiments, a cap includes a pressurizing component and/or a cap body. A pressurizing component can be a protrusion, e.g., a cylindrical protrusion, extending from a surface, e.g., an interior surface, of the cap body. A pressurizing component can be integral with the cap body, e.g., composed of a single piece of material, or can be operatively coupled, e.g., adhesively coupled, thereto. In some versions, a pressurizing component is composed of the same material as the cap body and in other versions, the pressurizing component is composed of a different material than the cap body.

A pressuring component can include one or more biasing elements or materials which can be configured to deform from a first configuration to a second configuration and while in the second configuration, be biased to return to the first configuration. As described herein, biasing elements can deform from a first configuration to a second configuration when a cap is operatively coupled to a sample receiving module and while in the second configuration, be biased to return to the first configuration. A pressuring component can also return to a first configuration from a first configuration when a fluid is discharged from a sample receiving module. Biasing elements can exert force on a fluid in contact with the elements and can thereby pressurize the fluid.

A pressuring component according to the subject embodiments can be flexible. By "flexible," as used herein is meant pliable or capable of being bent or flexed repeatedly (e.g., bent or flexed with a force exerted by a human hand or other body part) without damage (e.g., physical deterioration). A pressuring component can also include one or more polymeric materials (e.g., materials having one or more polymers including, for example, plastic and/or rubber and/or foam) and/or metallic materials, such as metallic materials forming a spring.

A pressurizing component can be shaped as a cylinder, rectangular box, pyramid, cube, or any combination thereof. In embodiments where the pressurizing component is shaped as a cylinder, it can have a height ranging from 0.1 mm to 5 cm, such as 1 mm to 1 cm, such as 1 mm to 5 mm, inclusive. As used herein, "inclusive" refers to a provided range including each of the listed numbers. Unless noted otherwise herein, all provided ranges are inclusive. The pressurizing component can also have a height of 5 cm or less, such as 3 cm or less, such as 1 cm or less, such as 5 mm or less, such as 3 mm or less, such as 1 mm or less. The pressurizing component can also have a height of 1 mm or more, such as 3 mm or more, such as 5 mm or more, such as 1 cm or more, such as 3 cm or more, such as 5 cm or more. Such a pressurizing component can also have a diameter ranging from 1 mm to 5 cm, such as 1 mm to 3 cm, such as 1 mm to 1 cm, or 1 cm to 3 cm, each inclusive. Such a pressurizing component can also have a diameter of 5 cm or less, such as 3 cm or less, such as 1 cm or less, such as 5 mm or less, such as 3 mm or less, such as 1 mm or less. A pressurizing component can also have a diameter of 1 mm or more, such as 3 mm or more, such as 5 mm or more, such as 1 cm or more, such as 3 cm or more, such as 5 cm or more.

In versions where a pressurizing component is shaped as a rectangular box or a cube, the pressurizing component can have a length, width, and/or height of 5 cm or less, such as 3 cm or less, such as 1 cm or less, such as 5 mm or less, such as 3 mm or less, such as 1 mm or less. A pressurizing component can also have a length, width, and/or height of 1 mm or more, such as 3 mm or more, such as 5 mm or more, such as 1 cm or more, such as 3 cm or more, such as 5 cm or more. A pressurizing component can also have a length, width, and/or height ranging from 1 mm to 5 cm, such as 1 mm to 3 cm, such as 1 mm to 1 cm, or 1 cm to 3 cm, each inclusive.

A pressurizing component can also be configured to extend into, such as fully into, and/or engage with, e.g., slidably and/or sealably engage with, a sample receiving module, or a portion thereof, such as a fluid container or a portion thereof, e.g., an internal surface defining the fluid container, when a cap is operatively coupled with the sample receiving module.

The subject disclosure also provides device embodiments wherein the pressurizing component extends into, e.g., extends fully into, and pressurizes the sample receiving module when the cap is operatively coupled to the sample receiving module, such as when a first attachment element is operatively coupled to a second attachment element. The pressure can be applied, for example, for expelling fluid from the sample receiving module. When desired, the sample receiving module or a fluid container thereof is sealed when the pressurizing component is inserted and extends therein.

The pressurizing component pressurizes the sample receiving module by exerting force on one or more fluid, e.g., a liquid and/or gas, within the sample receiving module, such as air and/or preparation solution. As the pressurizing component extends further into the sample receiving module, the pressure increases because the pressurizing component exerts more force on the one or more fluid. When the pressurizing component is retained in a particular position within the sample receiving module, the pressure in the module remains constant when the sample receiving module remains sealed.

In various embodiments, the pressurizing component pressurizes the sample receiving module to a pressure ranging from 50 Pa to 50,000 Pa, such as 500 Pa to 50,000 Pa, such as 1,000 Pa to 50,000 Pa, such as 5,000 Pa to 50,000 Pa, such as 10,000 Pa to 30,000 Pa, such as 15,000 Pa to 25,000 Pa, each inclusive. Where desired, the pressurizing component pressurizes the sample receiving module to a pressure of 1,000,000 Pa or less, such as 50,000 Pa or less, such as 30,000 Pa or less, such as 10,000 Pa or less, such as 5,000 Pa or less, such as 1,000 Pa or less, such as 500 Pa or less, such as 50 Pa or less. In some versions, the pressurizing component pressurizes the sample receiving module to a pressure of 1,000,000 Pa or more, 50,000 Pa or more, 30,000 Pa or more, 10,000 Pa or more, or 5,000 Pa or more, 1,000 Pa or more, 500 Pa or more, or 50 Pa or more.

In some embodiments, caps include one or more receptacle therein. Caps can include an outer surface and an interior surface defined by the one or more receptacle. Such a receptacle can extend inwardly from an opening, e.g., a circular opening, in a single flush and flat surface, e.g., a circular surface, of a cap. A receptacle can be configured to receive therein, e.g., entirely therein, one or more portions of a sample receiving module, e.g., an end of a sample receiving module and/or one or more portions of a preparation solution of a sample receiving module and/or one or more seal of a sample receiving module and/or one or more attachment elements of a sample receiving module, when the cap is operatively coupled to the sample receiving module. In some versions, a terminal end surface of a sample receiving module contacts and/or is flush against a surface of a cap, such as an internal surface, e.g., a terminal internal surface, of a cap receptacle, when the cap is operatively coupled to the sample receiving module. A cap can also seal, e.g., fluidically seal, a fluid container of a sample receiving module when the cap is operatively coupled to the sample receiving module. A receptacle can be shaped as a cylinder, rectangular box, pyramid, cube, or any combination thereof.

In embodiments where the receptacle is shaped as a cylinder, it can have a height ranging from 0.1 mm to 5 cm, such as 1 mm to 1 cm, such as 1 mm to 5 mm, inclusive. The receptacle can also have a height of 5 cm or less, such as 3 cm or less, such as 1 cm or less, such as 5 mm or less, such as 3 mm or less, such as 1 mm or less. The receptacle can also have a height of 1 mm or more, such as 3 mm or more, such as 5 mm or more, such as 1 cm or more, such as 3 cm or more, such as 5 cm or more. Such a receptacle can also have a diameter ranging from 1 mm to 5 cm, such as 1 mm to 3 cm, such as 1 mm to 1 cm, or 1 cm to 3 cm, each inclusive. Such a receptacle can also have a diameter of 5 cm or less, such as 3 cm or less, such as 1 cm or less, such as 5 mm or less, such as 3 mm or less, such as 1 mm or less. A receptacle can also have a diameter of 1 mm or more, such as 3 mm or more, such as 5 mm or more, such as 1 cm or more, such as 3 cm or more, such as 5 cm or more. A receptacle can also define an internal volume ranging from 1 $mm^3$ to 50 $cm^3$, from 1 $mm^3$ to 10 $cm^3$, from 1 $mm^3$ to 5 $cm^3$, such as from 5 $mm^3$ to 3 $cm^3$, such as from 5 $mm^3$ to 1 $cm^3$. A receptacle can also define an internal volume of 1 $mm^3$ or more, such as 5 $mm^3$ or more, 1 $cm^3$ or more, or 10 $cm^3$ or more. A receptacle can also define an internal volume of 50 $cm^3$ or less, such as 10 $cm^3$ or less, such as 5 $cm^3$ or less, such as 1 $cm^3$ or less or 5 $mm^3$ or less.

In some versions of the subject embodiments, a pressurizing component is disposed within, e.g., entirely within, a receptacle of a cap. In some embodiments, a pressurizing component can extend from a circular end surface of a cylindrical receptacle toward an opposite open end of the cylindrical receptacle.

Also, in some embodiments, caps include one or more attachment element. Such an element can be disposed within, e.g., entirely within, a receptacle of a cap. Such an element can also be disposed on an exterior surface of a cap. An attachment element can be configured to operatively couple the cap with a sample receiving module. Such an attachment element can specifically include one or more engagement elements for mateably coupling with a sample receiving module. In some versions, an attachment element can include a screwable thread and/or a thread track or groove, for screwing to a reciprocating thread or thread track or groove. Attachment elements according to the subject embodiments can also include one or more releasing element for releasing one attachment from another and which can include one or more button and/or lever and/or switch. Attachment elements, e.g., a second attachment element, can extend around, e.g., concentrically around, a pressurizing component of a device. Attachment elements, e.g., a second attachment element, can also be exclusively inside, e.g., on an internal surface of, a cap or a portion thereof, e.g., a cap body. In other words, all portions of an attachment element can fall between at least two other portions of the cap, e.g., cap body.

According to the subject embodiments, the sample receiving modules and/or caps or portions thereof, e.g., pressurizing components, can each be composed of a variety of materials and can be composed of the same or different materials. The sample receiving modules and/or caps or portions thereof can be composed of polymeric materials (e.g., materials having one or more polymers including, for example, plastic and/or rubber) and/or metallic materials. Such materials can have characteristics of flexibility and/or high strength (e.g., able to withstand significant force, such as a force exerted on it by use, without breaking and/or resistant to wear) and/or high fatigue resistance (e.g., able to retain its physical properties for long periods of time regardless of the amount of use or environment).

Materials of interest of which any of the device components described herein can be composed include, but are not limited to: polymeric materials, e.g., plastics, such as polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, etc., metals and metal alloys, e.g., titanium, chromium, stainless steel, etc., and the like.

According to some embodiments, the subject devices and components thereof, e.g., sample receiving modules and/or caps, are hand-held devices. As used herein, the term "hand-held" refers to the characteristic ability of an aspect to be held (e.g., retained, or easily or comfortably held) in a hand, such as the hand of a mammal, such as the hand of a human, such as the hand of an adult male or female human of an average size and/or strength. As such, a hand-held aspect is an aspect that is sized and/or shaped to be retained (e.g., easily or comfortably retained) in the hand of a human. A hand-held aspect can also be an aspect that can be moved (e.g., easily moved, such as easily moved in a vertical and/or horizontal direction) by a human (e.g., one or two hands of a human).

As noted above, in some versions, the subject devices can include a variety of optional components, any one or combination of which can be included in the devices, including a filter for filtering one or more fluids passing through a valve. The filter can be a porous membrane and/or a gel and/or a sponge material and can be selectively permeable. Such a filter can have a porosity such that it filters cellular components, such as cellular membranes from a prepared sample when the prepared sample flows through the filter. The filter can also have a porosity such that it traps and/or concentrates particles, e.g., bacteria, from a sample. As such, the subject methods as provided below can include concentrating one or more particles, e.g., particles in a sample fluid, by flowing a liquid, e.g., a sample fluid, through the filter. The filter can also be modified to bind to nucleic acids or proteins for downstream elution. A filter can have a pore size ranging from 1 µm to 100 µm, 1 µm to 50 µm, 1 µm to 25 µm, 1 µm to 15 µm, such as 1 µm to 10 µm, such as 1 µm to 5 µm, or 100 µm or less, or 50 µm or less, or 15 µm or less or 10 µm or less or 5 µm or less. A filter can also be mounted within, e.g., entirely within, a wall of a sample receiving module and can be at an end of a sample receiving module opposite an end operatively connectable to a cap. Filters, according to the subject embodiments, can be part of or positioned within the one or more valves described herein.

Embodiments of the disclosed devices also include a first seal e.g., a breakable seal and/or a frangible seal, for sealing an opening at an end of the sample receiving module through which fluid can flow out of the module via the valve. The seal can be positioned between, such as between in a path of fluid flow when fluid is flowing out of the sample receiving module, a filter and a valve, as such components are described herein. A first seal can be punctured by actuating a valve of a pressurized sample receiving module. Pressurized fluid from a pressurized sample receiving module can exert sufficient force on a seal to break it and flow through the created opening.

Some embodiments of the disclosed devices also include a second seal e.g., a breakable seal and/or a frangible seal, for sealing an opening at an end of the sample receiving module which operatively couples to a cap. A second seal can provide a fluidic seal to a fluid container. Such a seal can be broken by exerting force on it with a sample collector and thus creating an opening in the seal through which the sample collector or a portion thereof can be inserted. A second seal can also be broken by operatively coupling a cap to a sample receiving module. Such an action can cause a pressurizing component to exert sufficient force on the seal to puncture it.

A seal, such as a first and/or second seal, can be a layer of material, such as a polymeric and/or metallic material as such materials are described herein. In some versions, a seal is a foil sheet composed of aluminum and/or other metals. A seal, as described herein, can have a thickness of 1 mm or less, such as 0.5 mm or less, such as 0.1 mm or less.

Figure 2:
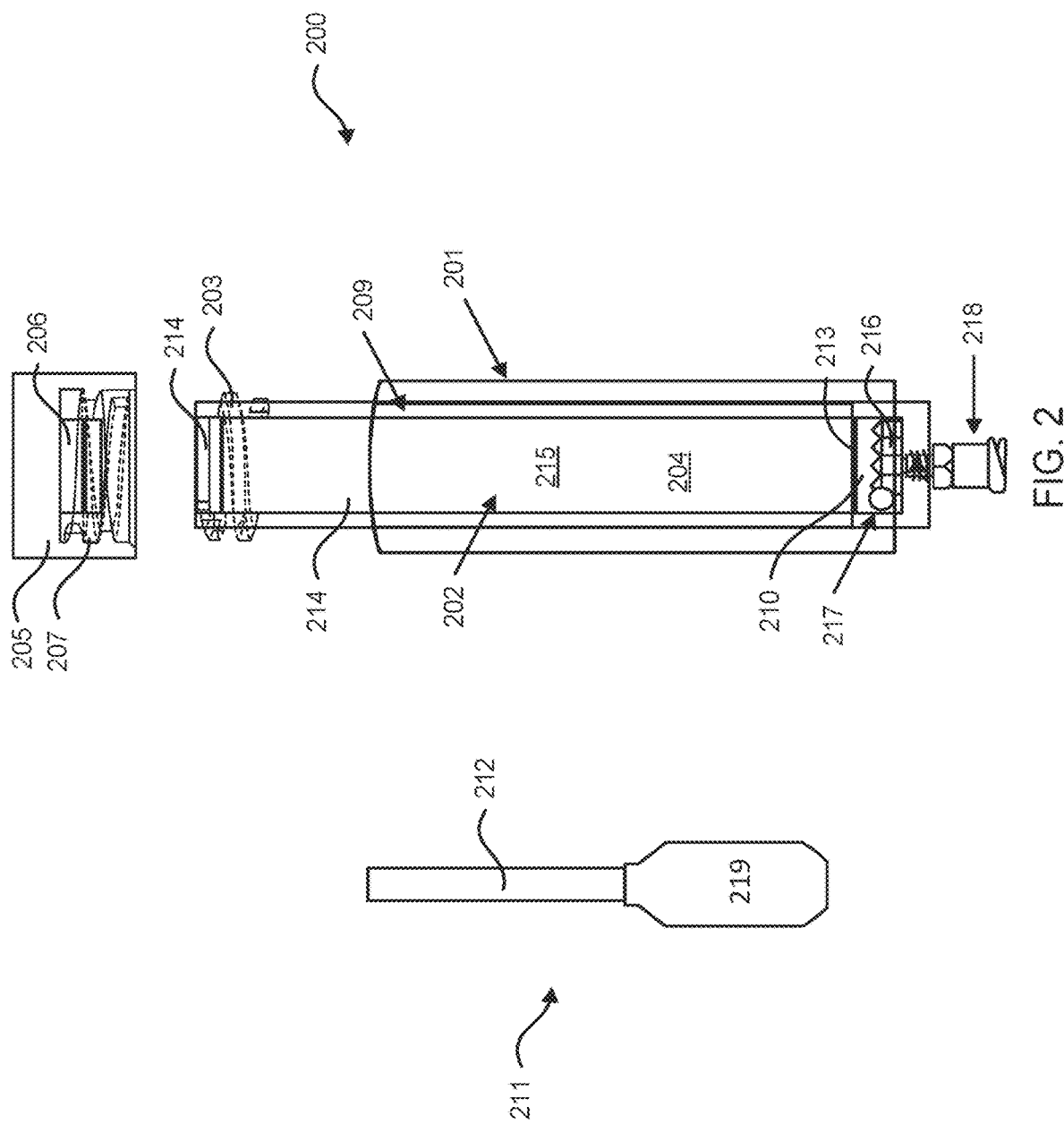
FIG. 2 provides a partial cross sectional view of a device according to embodiments of the present disclosure.

An embodiment of a biological assay sample preparation device is provided in FIG. 2. As is shown, in some versions, the device 200 includes a sample receiving module 201 including an outer body 209 forming a first chamber 210. The sample receiving module 201 also includes a fluid container 202 for receiving one or more portions of a sample collector 211 therein, e.g., entirely therein, a preparation solution 204, and a first attachment element 203. As shown, in some versions, the fluid container 202 includes a breakable seal 213 and an inner body 214 forming a second chamber 215, wherein the inner body 214 is actuable, e.g., slidable, within the outer body 209.

As is shown, the sample collector includes a handle 212 and a sample collection portion 219. Such a device 200 can also include a cap 205 operatively, e.g., removably, coupleable to the sample receiving module 201 and including a pressurizing component 206, and a second attachment element 207 operatively coupleable with the first attachment element 203. In some embodiments of the devices, the pressurizing component 206 extends into and pressurizes the sample receiving module 201 for expelling fluid therefrom when the first attachment element 203 is operatively coupled to the second attachment element 207.

In some versions, the outer body 209 includes one or more piercing member 216. Also, in some aspects, the inner body 214 actuates within the outer body 209 when the cap 205 is operatively coupled to the sample receiving module 201 to break the breakable seal 213 with the one or more piercing member 216 and place the first chamber 210 in fluidic communication with the second chamber 215. Such actuation can be in a direction, e.g., a linear direction along an axis of symmetry of the device, toward the one or more piercing member 216 and/or valve 218 and/or away from the cap 205. In some versions, the outer body 209 includes a staging reagent 217 and such actuation places the staging reagent 217 in fluidic communication with the second chamber 215. In some aspects, the staging reagent 217 includes one or more lyophilized agents, such as one or more lyophilized cell lysing reagent, and placing the staging reagent 217 in fluidic communication hydrates the reagent with the preparation solution 204 and/or exposes the staging reagent 217 to the biological sample. Additionally, in some versions, a cap 205 and/or valve 217 are centered on an axis of symmetry of the sample receiving module 201 when the module 201 is operatively coupled to the cap 205.

As used herein, a reagent or agent is a composition for use in the subject assays. Reagents or agents can be a liquid composition which is configured to change, e.g., chemically and/or physically modify, one or more aspects of a biological sample or an aspect thereof upon contact with the sample or aspect. Also, as used herein, staging reagents are reagents that prepare a biological sample for further processing as described herein. Such reagents can be lysing agents and can be configured to create a lysate. In various embodiments, the one or more staging reagents 217 include dichlorodiphenyl-trichloroethane (DDT), dithiothreitol (DTT), detergents, e.g., TRITON X-100™, TWEEN®, Sodium dodecyl sulfate (SDS), chaotropic salts, acids and/or bases, pH buffers, beads, solvents, or any combinations thereof.

Figure 3:
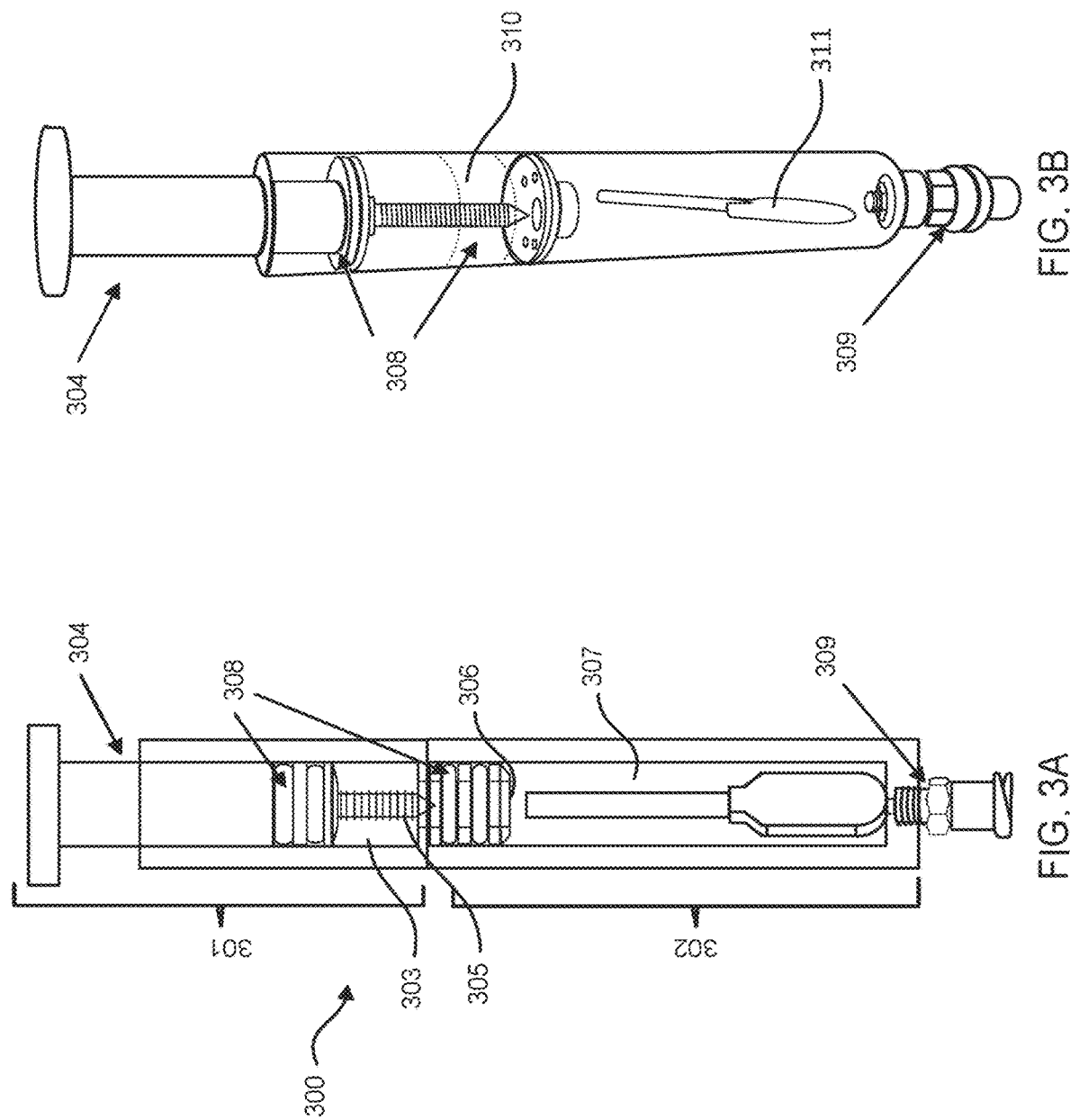
FIGS. 3A and 3B provide side views of devices according to embodiments of the subject disclosure.

In some versions of the subject devices, the devices include one or more plunger. Such a device is shown, for example, in FIGS. 3A, 3B and 4. Specifically, provided in these figures is a biological assay sample preparation device 300 including a cap 301 and a sample receiving module 302 which is operatively coupleable to the cap 301. As depicted, the cap 301 can include a first chamber 303, a plunger 304 including a piercing member 305, and/or a seal 306. In various embodiments, the first chamber 303 includes a preparation solution 310, such as any of the solutions described herein. Also, the sample receiving module 302 can include a second chamber 307. The second chamber 307 can be configured to receive and/or retain a sample collector 311 therein. The second chamber 307 can also include solution, such as a preparation solution and/or water and/or one or more buffer.

The cap can include a preparation solution 310 in an amount ranging from 500 μL to 1500 μL, such as from 700 μL to 1,000 μL, such as from 700 μL to 900 μL. The cap can include a preparation solution in an amount of 1500 μL or less, such as 1,000 μL or less, such as 800 μL or less. The cap can include a preparation solution in an amount of 600 μL or more, such as 800 μL or more, such as 1,000 μL or more. The cap can include a preparation solution in an amount of 800 μL. Also, in some embodiments, the preparation solution is a buffer, such as a cell lysis buffer, and can include one or more detergents.

In some versions, when the sample receiving module 302 is operatively coupled to the cap 301, advancing the plunger 304 pierces the seal 306 with the piercing member 305 and places the first chamber 303 in fluidic communication with the second chamber 307. As is also shown, the plunger can include one or more, e.g., two, or four, or more, O-rings 308 for sealably actuating the plunger 304 within the cap 301 and/or operatively coupling the cap 301 and the sample receiving module 302. The device 300 can also include one or more actuable valve 309 on the sample receiving module 302.

Figure 4:
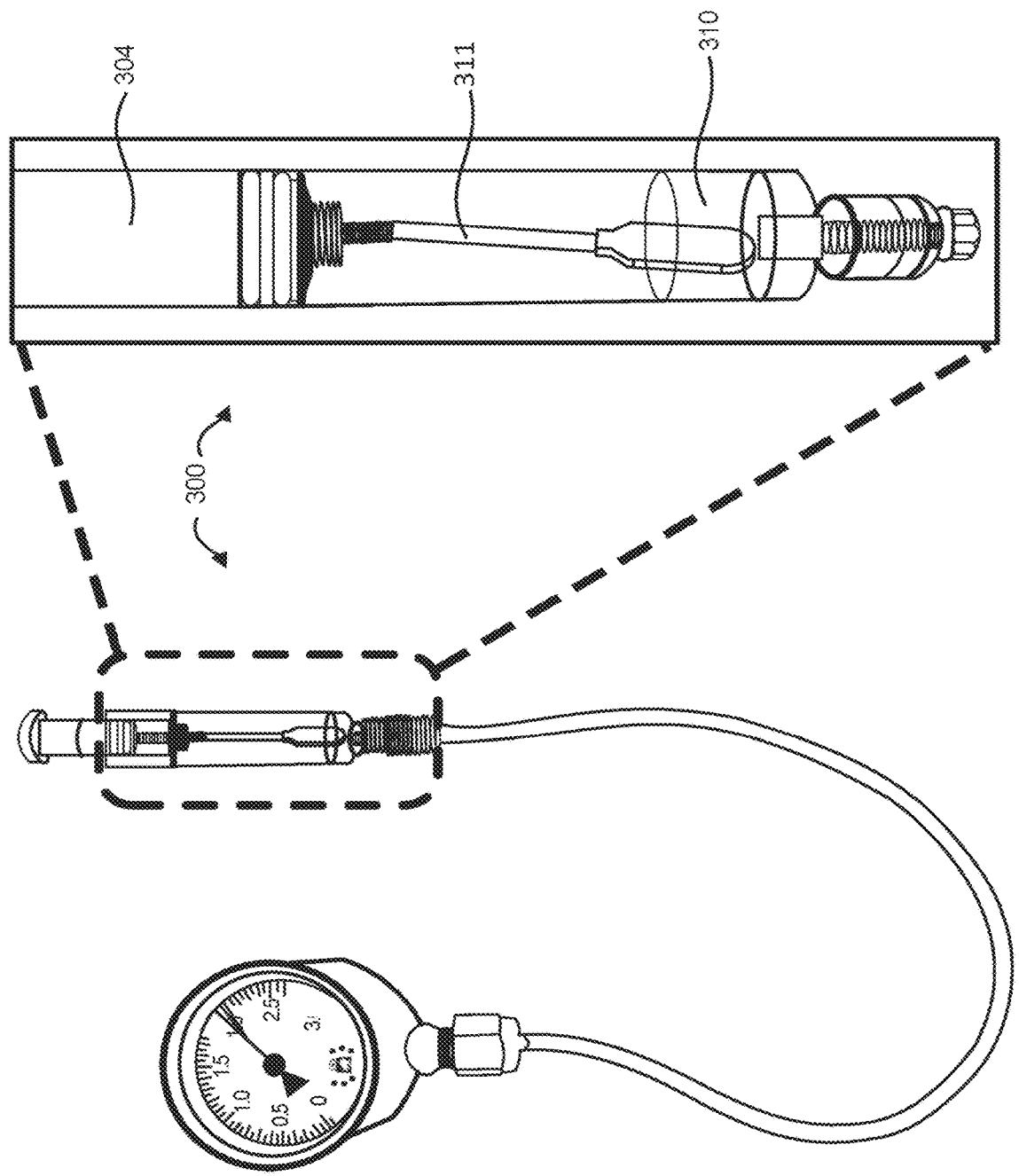
FIG. 4 provides side views of a device according to embodiments of the present disclosure.

The plunger 304 can also be a manual plunger which actuates within the first chamber 303 linearly along an axis of symmetry of the sample receiving module 302 and/or in a direction toward and/or away from a valve 309 of the device. Such a plunger 304 can be pushable directly by a user to increase pressure within the second chamber 307. The plunger 304 is shown in FIG. 4 in an advanced conformation where the plunger 304 has pushed the preparation solution 310 from the first chamber 303 into the second chamber 307. As is depicted, the plunger 304 is actuable, e.g., slidably actuable, within the cap 301 with respect to other portions of the cap 301, e.g., the cap body or housing, and as such, can move independently of the other portions. Also, as is shown, the plunger 304 is actuable, e.g., slidably actuable, within the cap 301 after the cap is first operatively coupled with the sample receiving module 302. Accordingly, operatively coupling the sample receiving module 302 and the cap 301 and then actuating the plunger 304 can be performed as two and separate steps with the subject device 300.

The user action of pressing the top of the cap 301, once it is sealed to the sample receiving module 302 forces the plunger 304 to break the seal 306 at the bottom of the cap 301, and exposes the sample collector 311 to the preparation solution 310. The pressure required for driving fluid flow is generated by the depression of the plunger 304 within the cap 301. This user action compresses fluid, e.g., preparation solution and/or biological sample, and/or air, inside the cap 301, leading to pressure generation. Subsequently, a valve 309, e.g., a luer-activated valve, of the device can be actuated and fluid, e.g., prepared sample and/or preparation solution and/or air, propelled by the pressure therethrough and out of the device. Alternatively, a valve 309 of the device can be replaced by a seal (not shown), e.g., a foil seal, e.g., a foil heat seal, which can be broken to allow fluid, e.g., prepared sample and/or preparation solution and/or air, propelled by the pressure to pass therethrough and out of the device. In other embodiments, a seal covers valve 309 and is ruptured by application of pressure or by a puncturing mechanism as described below.

The plunger 304 can be configured to reversibly actuate within the first chamber 303, such as by actuating in a first direction and/or actuating in a second direction opposite the first. Advancing the plunger 304 can pressurize the sample receiving module 302 or portion thereof, e.g., second chamber 307, to a pressure ranging from 50 Pa to 50,000 Pa, 500 Pa to 50,000 Pa, 1,000 Pa to 50,000 Pa, or 5,000 Pa to 50,000 Pa, such as 10,000 Pa to 40000 Pa, such as 15,000 Pa to 25,000 Pa, each inclusive. Where desired, the plunger pressurizes the sample receiving module to a pressure of 1,000,000 Pa or less, such as 50,000 Pa or less, such as 40000 Pa or less, such as 10,000 Pa or less, such as 5,000 Pa or less. In some versions, the plunger pressurizes the sample receiving module to a pressure of 1,000,000 Pa or more, 50,000 Pa or more, 40000 Pa or more, 10,000 Pa or more, or 5,000 Pa or more.

In addition, any of the components of FIG. 3A, 3B, 4, 5A or 5B, such as the plunger 304, can be composed of any of the polymeric and/or metallic materials described herein, or any combinations thereof. Also, the plunger 304 is shown, for example, in FIG. 4 in an advanced conformation wherein the plunger 304 has pushed the preparation solution 310 from the first chamber 303 into the second chamber 307.

Figure 5A:
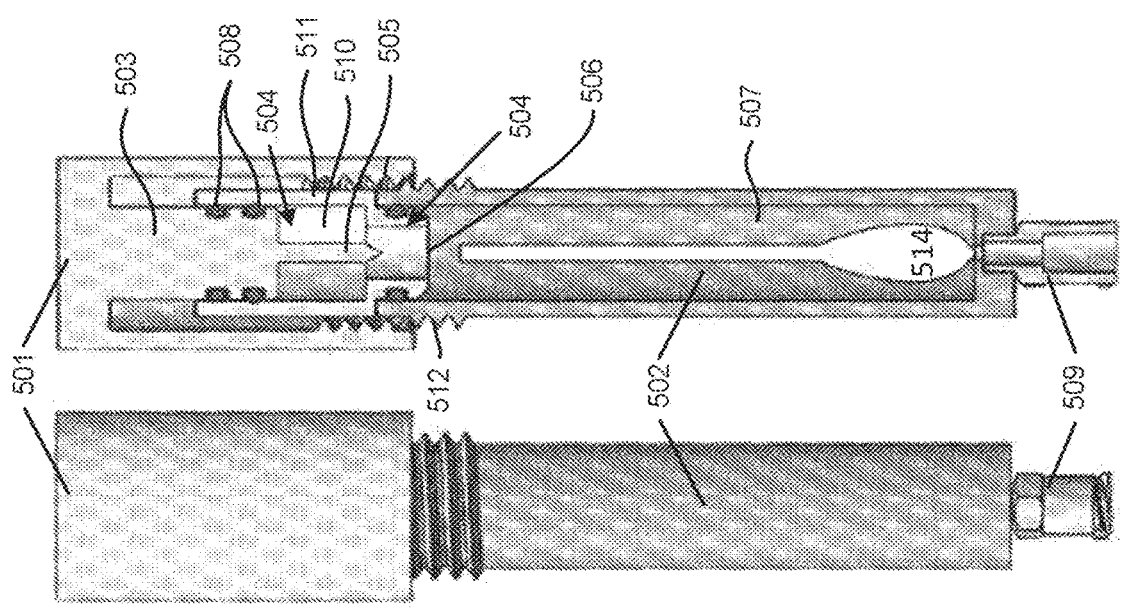

In some versions of the subject devices, such as the device shown in FIGS. 5A and 5B, the device 500 includes one or more plunger 503 of a cap 501 which is advanced by operatively coupling, such as by screwing, the cap 501 to a sample receiving module 502. More specifically, FIG. 5A provides both side and cross-sectional side views of the device 500 in a first conformation wherein the plunger 503 is substantially un-advanced within the device 500. FIG. 5B provides both side and cross-sectional side views of the device 500 in a second conformation wherein the plunger 503 is fully advanced within the device 500.

Operatively coupling the sample receiving module 502 and the cap 501 and actuating the plunger 503 can be performed as a single concerted step with the subject device 500. In other words, operatively coupling the sample receiving module 502 and the cap 501 also advances the plunger 503 of the device 500, such as advances the plunger from the first conformation to the second conformation. Also, as is depicted, the plunger 503 is integral with at least some portions of the cap, e.g., a housing or exterior shell. In some versions, the cap 501 includes a stationary body portion 511 which sealably mates with the sample receiving module 502 and includes a protruding portion which extends into the sample receiving module 502 when the two are mated. The plunger 503, as well the portions of the cap other than the stationary body portion 511 are freely actuable, e.g., slidably actuable, with respect to and can move independently of the stationary body portion 511 when the plunger actuates. As is shown in FIGS. 5A and 5B, the stationary body portion 511 remains in a fixed position with respect to the sample receiving module 502 when the device advances from the first conformation to the second conformation.

The cap 501 of device 500 shown in FIGS. 5A and 5B also includes a first chamber 504, plunger 503, piercing member 505, and/or seal 506. In various embodiments, the first chamber 504 includes a preparation solution 510, such as any of the solutions described herein. Also, the sample receiving module 502 can include a second chamber 507. The second chamber 507 can be configured to receive and/or retain a sample collector 514 therein. The second chamber 507 can also include solution, such as a preparation solution and/or water and/or one or more buffer.

The cap can include a preparation solution in an amount ranging from 500 µL to 1500 µL, such as from 700 µL to 1,000 µL, such as from 700 µL to 900 µL. The cap can include a preparation solution in an amount of 1500 µL or less, such as 1,000 µL or less, such as 800 µL or less. The cap can include a preparation solution in an amount of 600 µL or more, such as 800 µL or more, such as 1,000 µL or more. The cap can include a preparation solution in an amount of 800 µL. Also, in some versions, the preparation solution is a buffer, such as a cell lysis buffer, and can include one or more detergents.

In some versions, advancing the plunger 503 by operatively coupling the sample receiving module 502 and the cap 501, such as by screwing the sample receiving module 502 and the cap 501, pierces the seal 506 with the piercing member 505 and places the first chamber 504 in fluidic communication with the second chamber 507. As is also shown, the plunger can include one or more, e.g., two, or four, or more, O-rings 508 for sealably actuating the plunger 304 within the cap 501. The device 500 can also include one or more actuable valve 509 on the sample receiving module 502.

The plunger 503 can also actuates within the first chamber 504 linearly along an axis of symmetry of the sample receiving module 502 and/or in a direction toward and/or away from a valve 509 of the device. Such a plunger 503 can be advance to increase pressure within the second chamber 507. The plunger 503 is shown in FIG. 5B in an advanced conformation where the plunger 503 has pushed the preparation solution 510 from the first chamber 504 into the second chamber 507.

The subject sample receiving module 502 can also include one or more first attachment element 512. Also, a cap 501 can include one or more second attachment element 513 for operatively, e.g., reciprocally, coupling with the first attachment element 512. Such attachment elements can be configured to operatively couple the cap 501 with the sample receiving module 502. In some versions, and as shown in FIGS. 5A and 5B, a first and/or second attachment element of a sample receiving module or a cap can each include a screwable thread and/or a thread track or groove, for screwing to a reciprocating thread or thread track or groove. In some versions, an attachment element, e.g., a first attachment element or a second attachment element, includes a thread and another, e.g., a second or a first, attachment element includes a reciprocating groove for slidably receiving the thread therein.

The plunger 503 can be configured to reversibly actuate within the first chamber 504, such as by actuating in a first direction and/or actuating in a second direction opposite the first. Advancing the plunger 503 can pressurize the sample receiving module 502 or portion thereof, e.g., second chamber 507, to a pressure ranging from 5,000 Pa to 50,000 Pa, such as 10,000 Pa to 40000 Pa, such as 15,000 Pa to 25,000 Pa, each inclusive. Where desired, the plunger pressurizes the sample receiving module to a pressure of 1,000,000 Pa or less, such as 50,000 Pa or less, such as 40000 Pa or less, such as 10,000 Pa or less, such as 5,000 Pa or less. In some versions, the plunger pressurizes the sample receiving module to a pressure of 1,000,000 Pa or more, 50,000 Pa or more, 40000 Pa or more, 10,000 Pa or more, or 5,000 Pa or more.

In various embodiments, a user action of turning the cap 501, after it is sealed to the sample receiving module 502, forces the plunger 503 to break the seal 506 at the bottom of the cap 501, and places the preparation solution 510 and the sample collector 514 in fluidic communication and in some embodiments, immerses the sample collector 514 in the preparation solution 510. According to some embodiments, the pressure required for driving fluid flow within device 500 is generated by the actuation of the plunger due to rotation of the cap 501 with respect to the sample receiving module 502. Such a user action compresses fluid, e.g., air and/or preparation solution and/or biological sample, inside the device 500, and causes pressure generation. Such pressure is maintained while the preparation solution reacts with the biological sample to produce a prepared sample. Subsequently, a valve 509, e.g., a luer-activated valve, of the device can be actuated and fluid, e.g., prepared sample and/or preparation solution and/or air, propelled by the pressure therethrough and out of the device. Alternatively, a valve 509 of the device can be replaced by a seal (not shown), e.g., a foil seal, e.g., a foil heat seal, which can be broken to allow fluid, e.g., prepared sample and/or preparation solution and/or air, propelled by the pressure to pass therethrough and out of the device. Also, in some embodiments, when the sample receiving module is operatively coupled to the cap, advancing the plunger pierces the seal with the piercing member and places the first chamber in fluidic communication with the second chamber.

Figure 6:
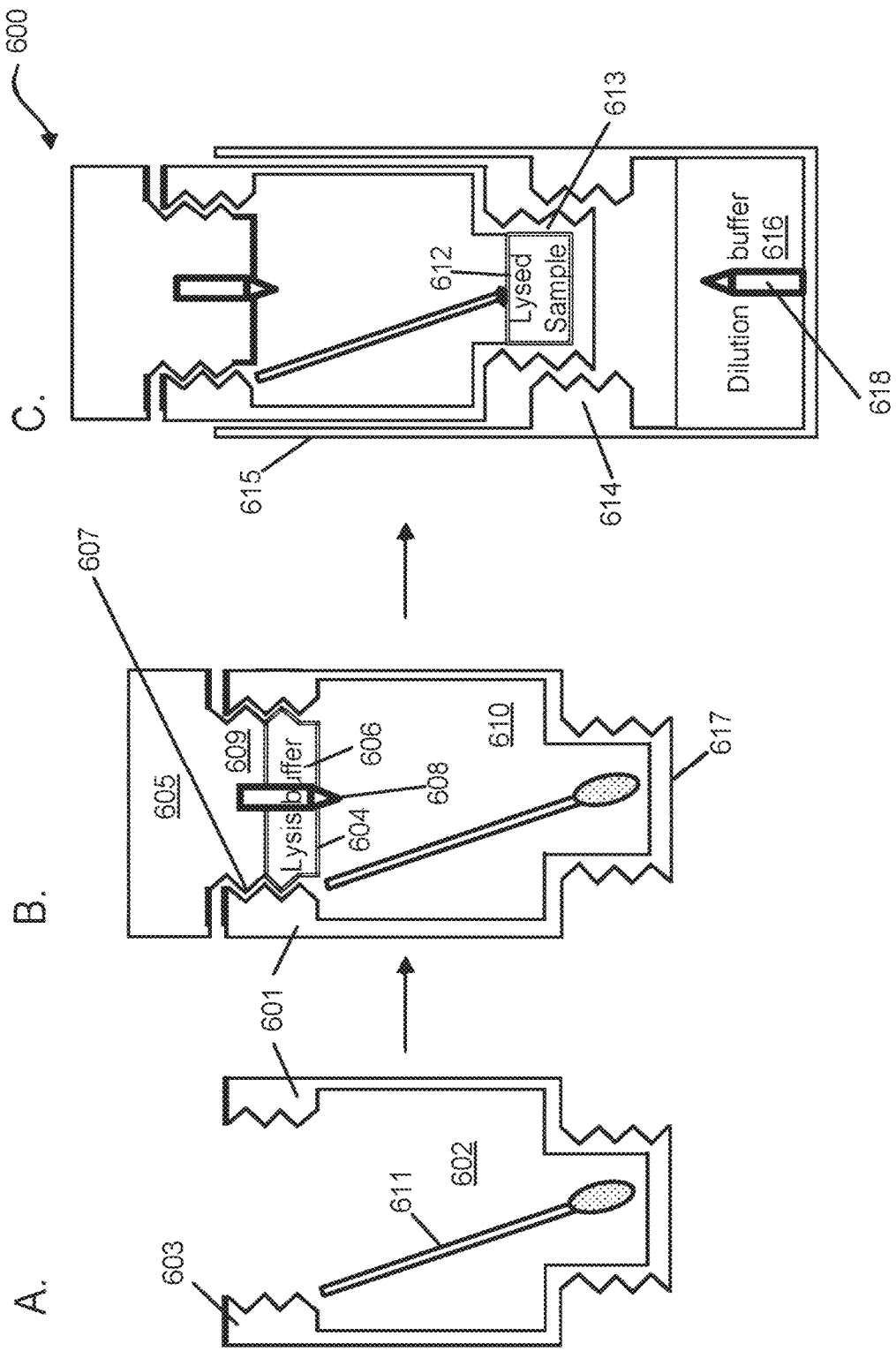
FIGS. 6A-C provide side cross sectional views of devices according to embodiments of the present disclosure.

An embodiment of a biological assay sample preparation device for use in practicing the subject methods is provided in FIGS. 6A-C. The provided device 600 includes a sample receiving module 601 including a fluid container 602 for receiving one or more portions of a sample collector 611 therein, e.g., entirely therein, and a first attachment element 603. Such a device 600 can also include a cap 605 operatively, e.g., removably, coupleable to the sample receiving module 601 and including a preparation solution, e.g., a lysis buffer 606, second attachment element 607 operatively coupleable with the first attachment element 603. The sample receiving module 601, cap 605 and other provided components can have any of the characteristics or combination of characteristics of sample receiving modules, caps and/or other corresponding components described herein.

In the embodiment shown, operatively coupling the sample receiving module 601 and the cap 605, as is shown in FIG. 6B, such as by screwing the sample receiving module 601 and the cap 605, pierces a seal 604 with a piercing member 608 and places a first chamber 609 in fluidic communication with a second chamber 610. As such, operatively coupling the sample receiving module 601 and the cap 605, such as by screwing the sample receiving module 601 and the cap 605 together, exposes preparation solution 606 to a sample on a sample collector 611 and thereby produces a prepared, e.g., lysed, sample 612.

Once the prepared, e.g., lysed, sample 612 is made, the sample receiving module 601 can be operatively coupled to a pressurizing module 615. Operatively coupling can be performed by attaching, such as by screwing, an attachment element 613 of a sample receiving module 601 and a second attachment element 614 of a pressurizing module 615. The pressurizing module 615 also includes a buffer, e.g., a dilution buffer 616. Operatively coupling the sample receiving module 601 and the pressurizing module 615, as is shown in FIG. 6C, places the prepared sample 612 in fluidic communication with the dilution buffer 616 so that the prepared sample 612 is diluted and pressurizes the sample receiving module. Thereafter, the diluted prepared sample can be delivered out of the device 600 for further analysis using the pressure within the device to push the diluted prepared sample out of the device 600.

Another embodiment of a biological assay sample preparation device for use in practicing the subject methods is provided in FIGS. 7A-D. The provided device 700 includes a sample receiving module 701 including a fluid container 702 for receiving one or more portions of a sample collector 711 therein, e.g., entirely therein, and a first attachment element 703. Such a device 700 can also include a cap 705 operatively, e.g., removably, coupleable to the sample receiving module 701 and including a preparation solution, e.g., a lysis buffer 706, second attachment element 707 operatively coupleable with the first attachment element 703. Operatively coupling the cap 705 and the sample receiving module 701 can pressurize the sample receiving module 701. The sample receiving module 701 can also include a buffer, e.g., a dilution buffer 718 in a buffer container 719 therein. The sample receiving module 701, cap 705 and other provided components can have any of the characteristics or combination of characteristics of sample receiving modules, caps and/or other corresponding components described herein.

Figure 7:
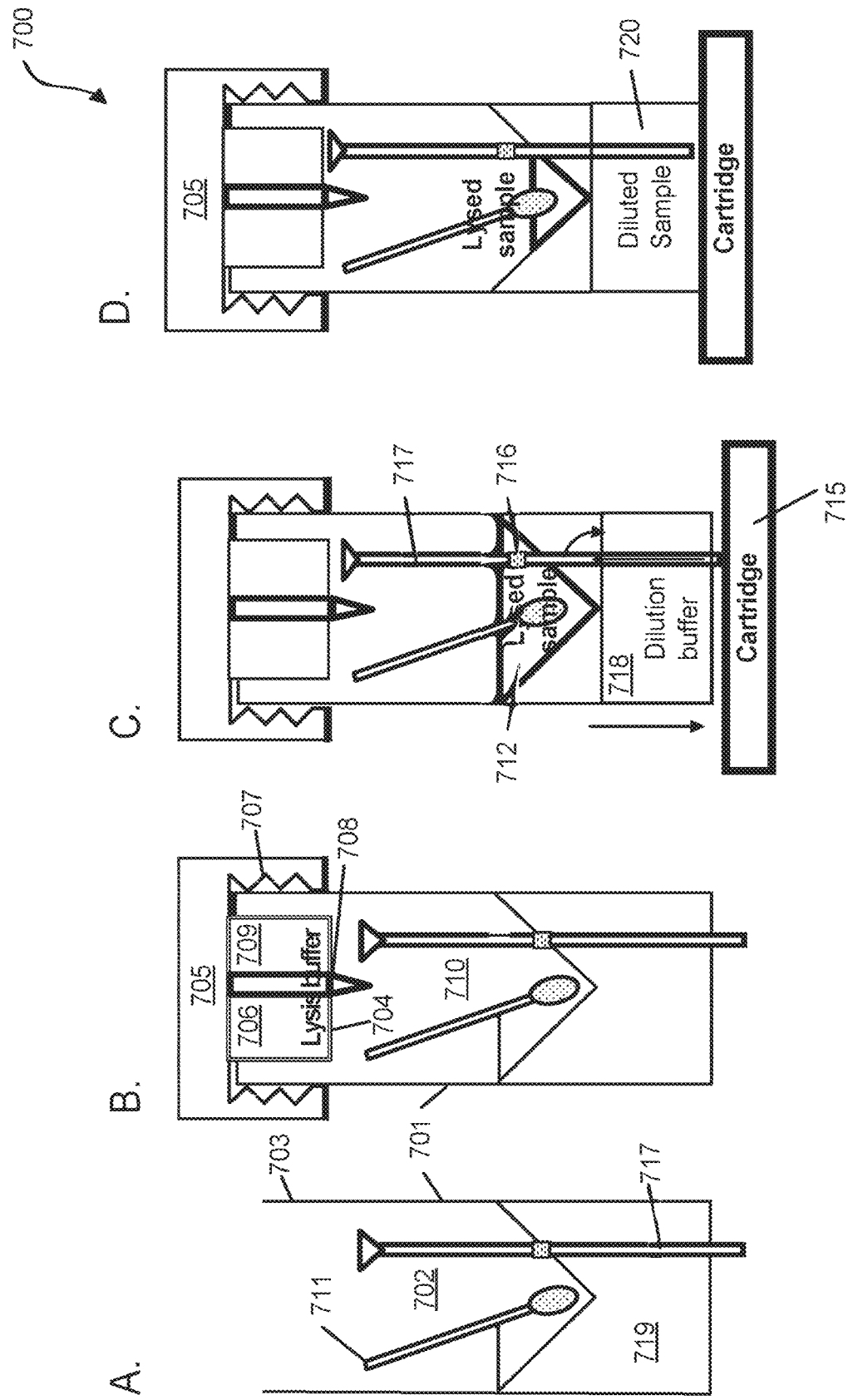
FIGS. 7A-D provide side cross sectional views of device aspects according to embodiments of the subject disclosure.

In the embodiment shown, operatively coupling the sample receiving module 701 and the cap 705, as is shown in FIG. 7B, such as by screwing the sample receiving module 701 and the cap 705, pierces a seal 704 with a piercing member 708 and places a first chamber 709 in fluidic communication with a second chamber 710. As such, operatively coupling the sample receiving module 701 and the cap 705, such as by screwing the sample receiving module 701 and the cap 705 together, exposes preparation solution 706 to a sample on a sample collector 711 and thereby produces a prepared, e.g., lysed, sample 712.

Once the prepared, e.g., lysed, sample 712 is made, the sample receiving module 701 can be operatively coupled to, such as by being lowered onto, a cartridge 715. Such operative coupling can actuate a fluidic communication element 717 and/or open a valve 716, e.g., poppet valve, of the fluidic communication element 717. The fluidic communication element 717 can be actuated toward the cap 705 when the cartridge 715 exerts force on it. Opening the valve 716 in turn releases the prepared sample 712 into the dilution buffer 718 in the buffer container 719 and produces a prepared diluted sample 720. Operatively coupling the sample receiving module 701 and the cartridge 715, as is shown in FIG. 7D, delivers the prepared diluted sample 720 out of the sample receiving module 703 and in to the cartridge.

One embodiment of a biological assay sample preparation device for use in practicing the subject methods is provided in FIGS. 8A-D. The provided device 800 includes a sample receiving module 801 including a fluid container 802 for receiving one or more portions of a sample collector 811 therein, e.g., entirely therein. Such a device 800 can also include a cap 805 operatively, e.g., removably, coupleable to the sample receiving module 801 and including a preparation solution, e.g., a lysis buffer 806.

Operatively coupling the cap 805 and the sample receiving module 801 may not pressurize the sample receiving module 801 but may place the lysis buffer 806 in fluidic communication with a sample on the sample collector 811 and thereby produce a prepared, e.g., lysed, sample 812. The sample receiving module 801, cap 805 and other provided components can have any of the characteristics or combination of characteristics of sample receiving modules, caps and/or other corresponding components described herein.

The device 800 also includes a pressurizing chamber 816 operatively coupled to the sample receiving module 801 and including a valve 817, e.g., a one-way valve, to provide fluidic communication therebetween. The pressurizing chamber 816 also includes a plunger 818, e.g., a manually actuable plunger, which creates positive and/or negative pressure within the pressurization chamber 816 when actuated. The pressurizing chamber 816 also includes a buffer, e.g., a dilution buffer 821. The pressurizing chamber 816 also includes an expulsion valve 819 for expelling a diluted prepared sample 820 therefrom upon actuation of the plunger 818.

Figure 8:
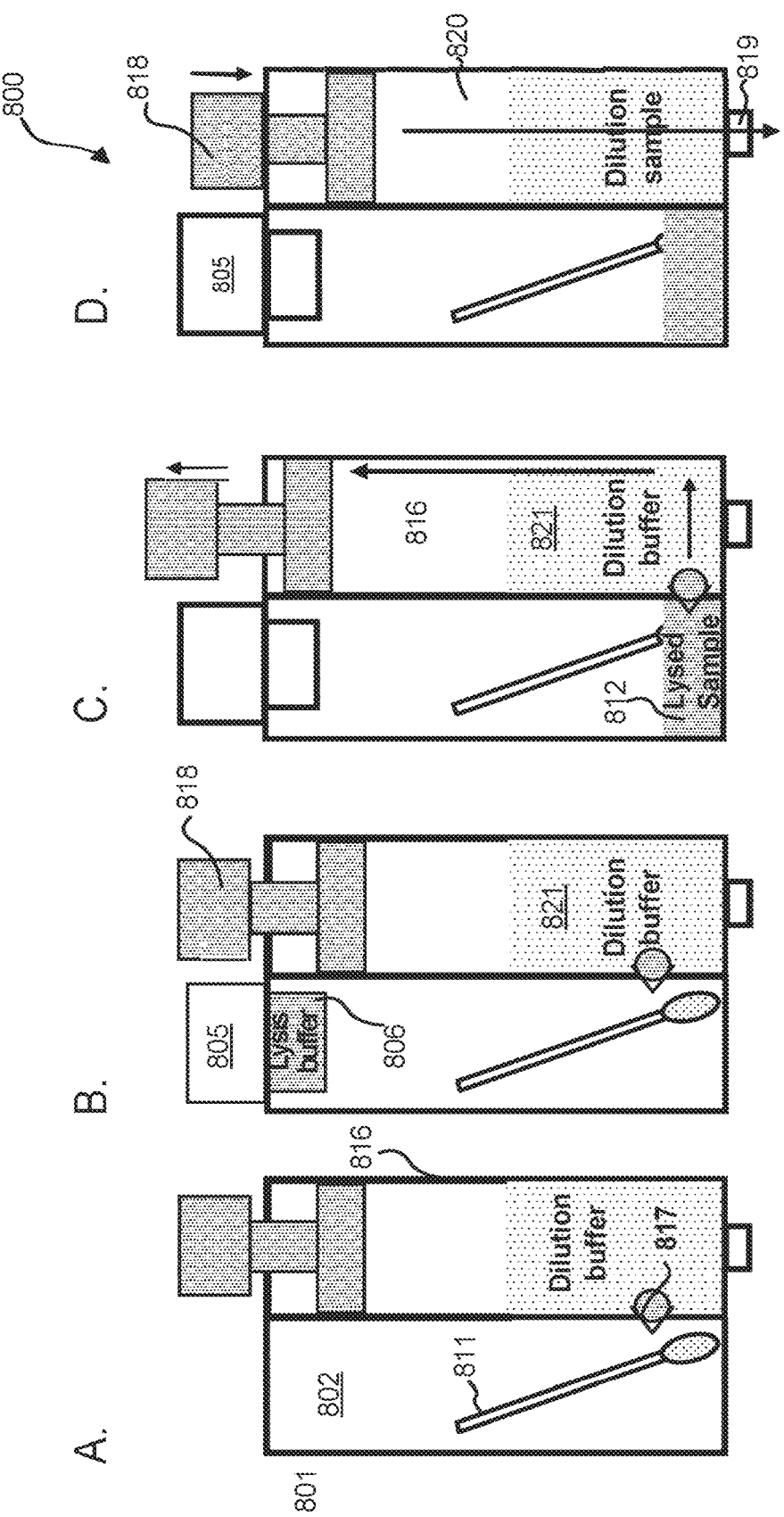
FIGS. 8A-D provide side cross sectional views of devices according to embodiments of the subject disclosure.

The device 800 is configured such that when the cap 805 is operatively coupled to the sample receiving module 801 to produce a prepared sample 812, the plunger 818 can be actuated in a first direction, as is shown in FIG. 8C, to propel the prepared sample 812 from the sample receiving module 801 and into the pressurizing chamber 816 via valve 817 and thereby produce a diluted prepared sample 820. The device 800 is also configured such that the plunger 818 can then be actuated in a second direction opposite the first, as is shown in FIG. 8D, to propel the diluted prepared sample 820 out of the pressurizing chamber 816 via expulsion valve 819.

Another embodiment of a biological assay sample preparation device for use in practicing the subject methods is provided in FIGS. 9A-D. The provided device 900 includes a sample receiving module 901 including a fluid container 902 for receiving one or more portions of a sample collector 911 therein, e.g., entirely therein. Such a device 900 can also include a cap 905 operatively, e.g., removably, coupleable to the sample receiving module 901 and including a preparation solution, e.g., a lysis buffer 906.

Operatively coupling the cap 905 and the sample receiving module 901 may not pressurize the sample receiving module 901 but may place the lysis buffer 906 in fluidic communication with a sample on the sample collector 911 and thereby produce a prepared, e.g., lysed, sample 912. The sample receiving module 901, cap 905 and other provided components can have any of the characteristics or combination of characteristics of sample receiving modules, caps and/or other corresponding components described herein.

The device 900 also includes a pressurizing chamber 916 operatively coupled to the sample receiving module 901 and including an opening, e.g., a vent 917, to provide fluidic communication therebetween. The pressurizing chamber 916 also includes a plunger 918, e.g., a manually actuable plunger, which creates positive and/or negative pressure within the pressurization chamber 916 when actuated. The pressurizing chamber 916 also includes a buffer, e.g., a dilution buffer 921. The pressurizing chamber 916 also includes an expulsion valve 919 for expelling a diluted prepared sample 920 therefrom upon actuation of the plunger 918.

Figure 9:
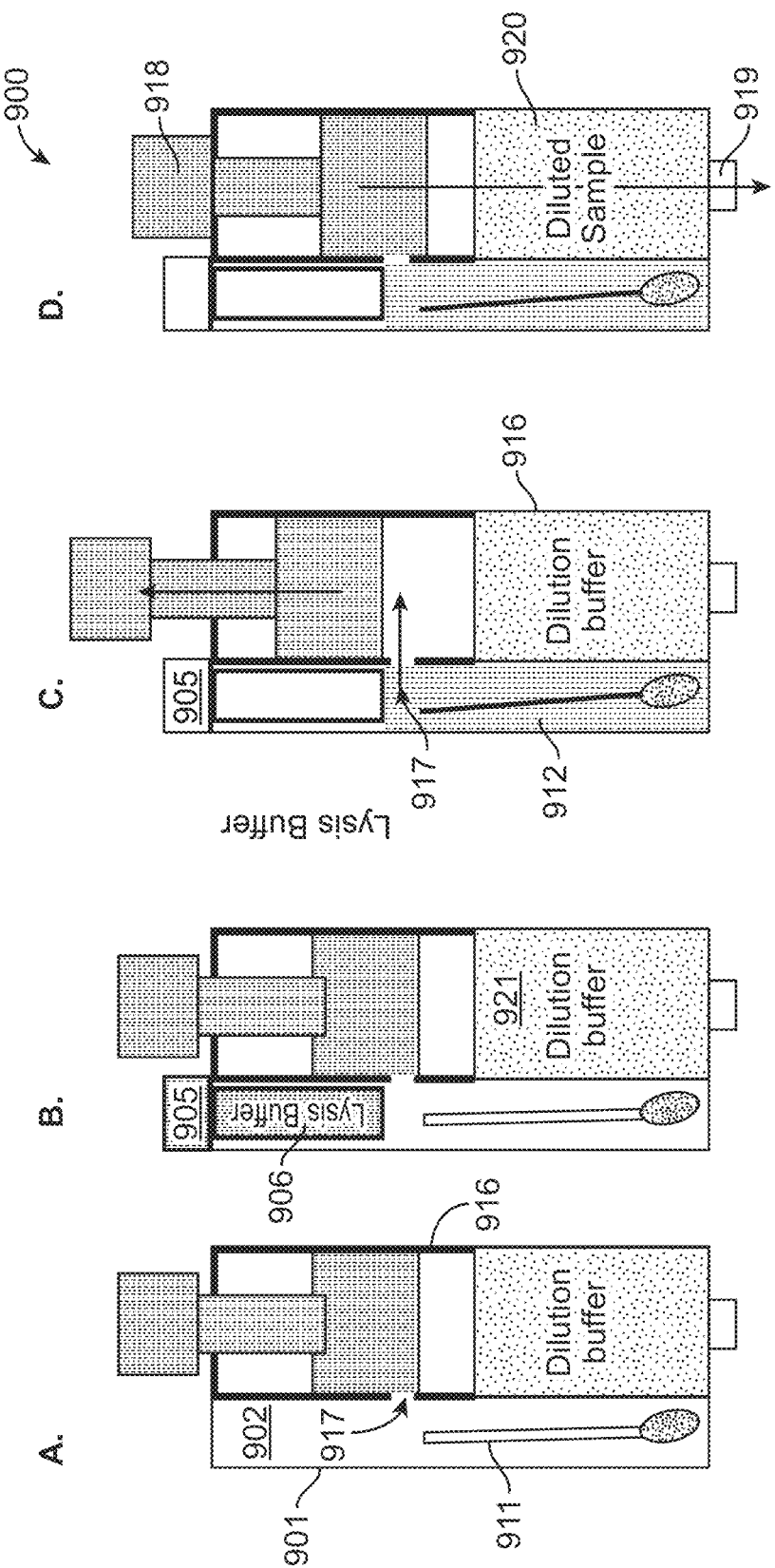
FIGS. 9A-D provide side cross sectional views of devices according to embodiments of the subject disclosure.

The device 900 is configured such that when the cap 905 is operatively coupled to the sample receiving module 901 to produce a prepared sample 912, the plunger 918 can be actuated in a first direction, as is shown in FIG. 9C, to propel the prepared sample 912 from the sample receiving module 901 and into the pressurizing chamber 916 via vent 917 and thereby produce a diluted prepared sample 920. Actuating the plunger 918 in such as direction can unseal the vent 917. The device 900 is also configured such that the plunger 918 can then be actuated in a second direction opposite the first, as is shown in FIG. 9D, to propel the diluted prepared sample 920 out of the pressurizing chamber 916 via expulsion valve 919. Actuating the plunger 918 in such as direction can seal the vent 917 and prevent further fluid communication therethrough.

Figure 10:
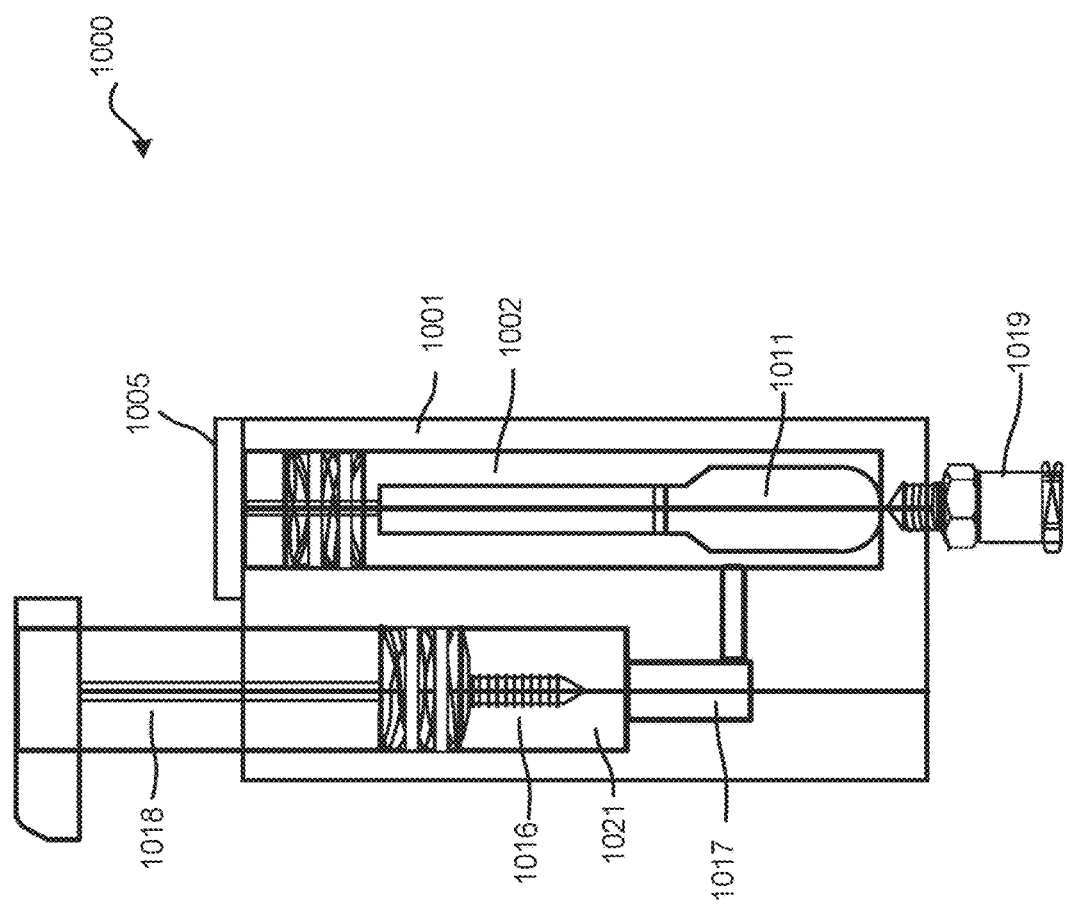
FIG. 10 provides a partial cross sectional view of a device according to embodiments of the present disclosure.

An embodiment of a biological assay sample preparation device for use in practicing the subject methods is provided in FIG. 10. The provided device 1,000 includes a sample receiving module 1001 including a fluid container 1002 for receiving one or more portions of a sample collector 1011 therein, e.g., entirely therein. Such a device 1,000 can also include a cap 1005 operatively, e.g., removably, coupleable to the sample receiving module 1001. The sample receiving module 1001, cap 1005 and other provided components can have any of the characteristics or combination of characteristics of sample receiving modules, caps and/or other corresponding components described herein. Operatively coupling the cap 1005 and the sample receiving module 1001 may not pressurize the sample receiving module 1001 but can place a preparation solution, e.g., a lysis buffer, in fluidic communication with a sample on the sample collector 1011 and thereby produce a prepared, e.g., lysed, sample.

The device 1,000 also includes a pressurizing chamber 1016 operatively coupled to the sample receiving module 1001 and including an opening, e.g., a channel 1017 including one or more containers, such as containers including one or more buffer, to provide fluidic communication therebetween. The pressurizing chamber 1016 can be oriented in parallel to the sample receiving module 1001, e.g., can both have a central axis of symmetry oriented in the same direction with respect to that of the other. The pressurizing chamber 1016 also includes a plunger 1018, e.g., a manually actuable plunger, which operates by pushing and/or pulling in a linear direction, and which creates positive and/or negative pressure within the pressurization chamber 1016 and/or sample receiving module 1001 when actuated. The pressurizing chamber 1016 also can include a buffer, e.g., a dilution buffer 1021. The sample receiving module 1001 also includes an expulsion valve 1019 for expelling a diluted prepared sample therefrom upon actuation of the plunger 1018.

The device 1,000 is configured such that the plunger 1018 can be actuated in a first direction, to propel a buffer from channel 1017 into the sample receiving module 1001 and thereby produce a diluted prepared sample therein and pressurize the sample receiving module. The diluted prepared sample can then be propelled by the pressure out of the sample receiving module 1001 via expulsion valve 1019.

Figure 11:
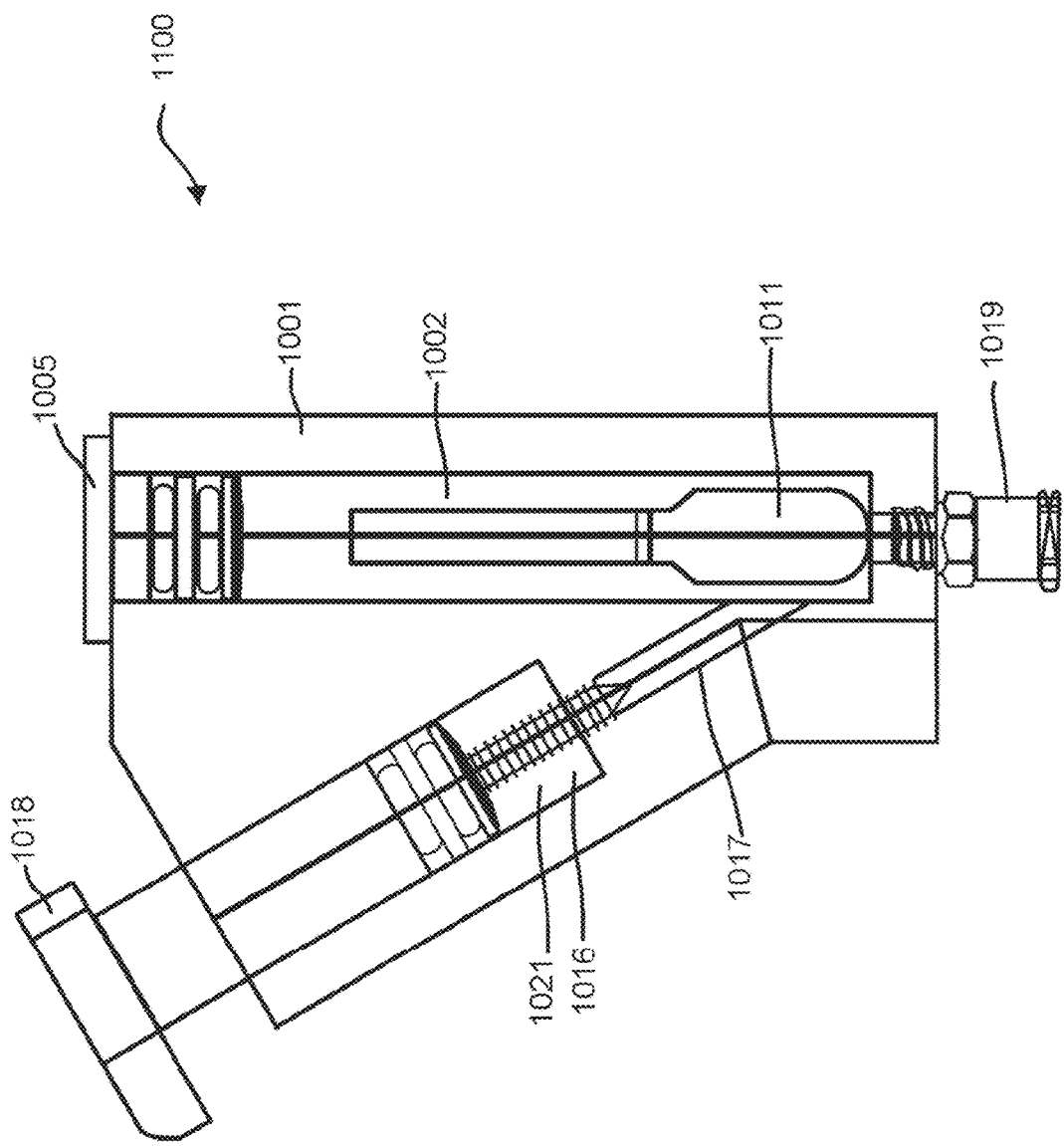
FIG. 11 provides a partial cross sectional view of a device according to some embodiments of the subject disclosure.

One embodiment of a biological assay sample preparation device for use in practicing the subject methods is provided in FIG. 11. The provided device 1100 includes many of the same components as the device shown in FIG. 10. However, the pressurizing chamber 1016 of the device 1100 of FIG. 11, can be oriented at an angle to the sample receiving module 1001, e.g., can both have a central axis of symmetry which intersects the other and/or is oriented at an angle, e.g., 30° or less, 45° or less, or 50° or less, or an angle ranging from 10° to 90°, inclusive, with respect to that of the other.

Figure 12:
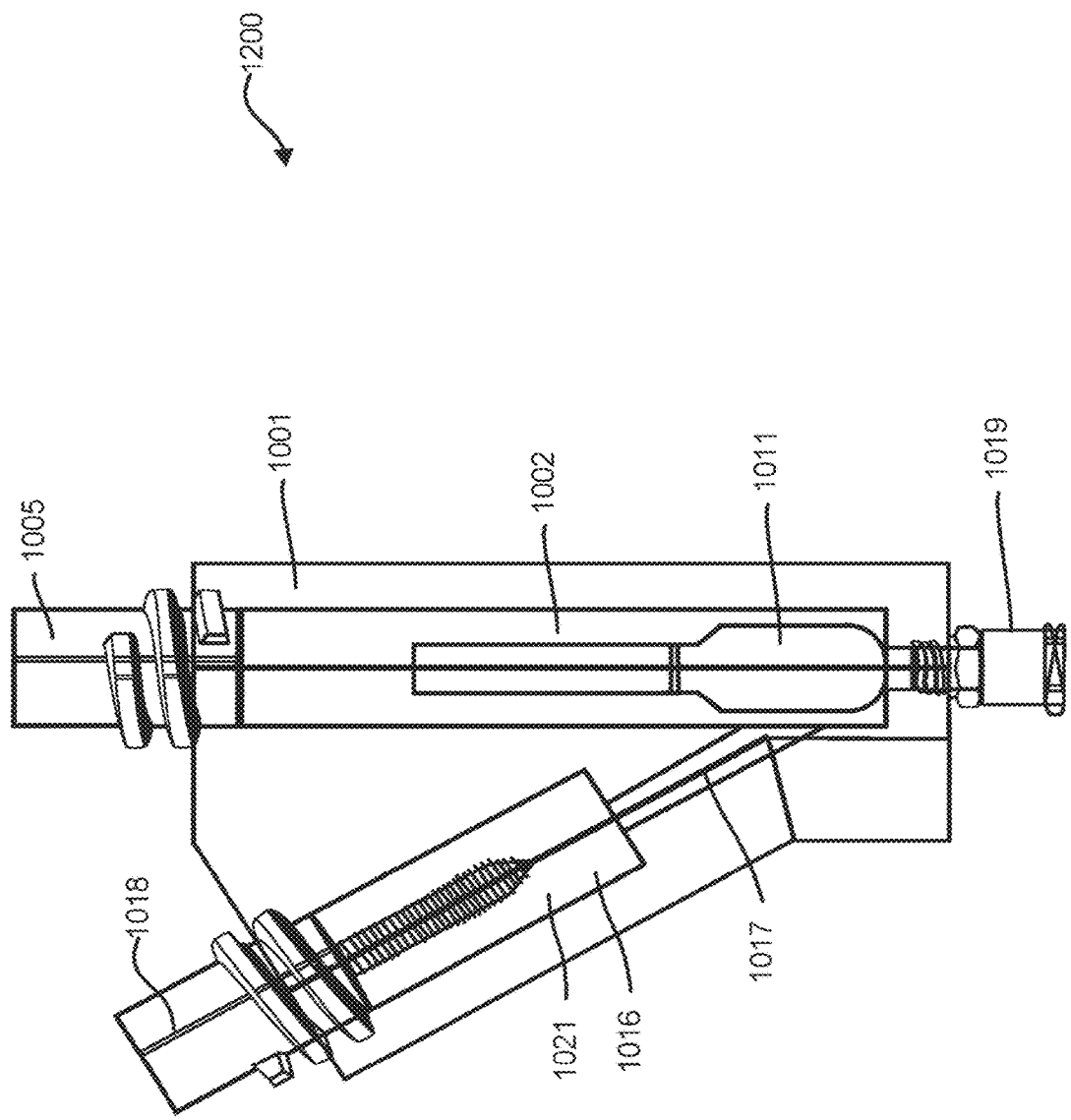
FIG. 12 provides a partial cross sectional view of a device according to embodiments of the present disclosure.

Another embodiment of a biological assay sample preparation device for use in practicing the subject methods is provided in FIG. 12. The provided device 1200 includes many of the same components as the devices shown in FIGS. 10 and 11. The pressurizing chamber 1016 can be oriented at an angle to the sample receiving module 1001, e.g., can both have a central axis of symmetry which intersects the other and/or is oriented at an angle, e.g., 30° or less, 45° or less, or 50° or less, or an angle ranging from 10° to 90°, inclusive, with respect to that of the other. Furthermore, the cap 1005 of the device 1200 is operatively coupleable to the sample receiving module 1001 by screwable attachment. Also, the plunger 1018 of the device 1200 is actuable by screwing it, such as by twisting it, further into the pressurizing chamber 1016 to pressurize the pressurizing chamber 1016 and/or the sample receiving module 1001.

Figure 13:
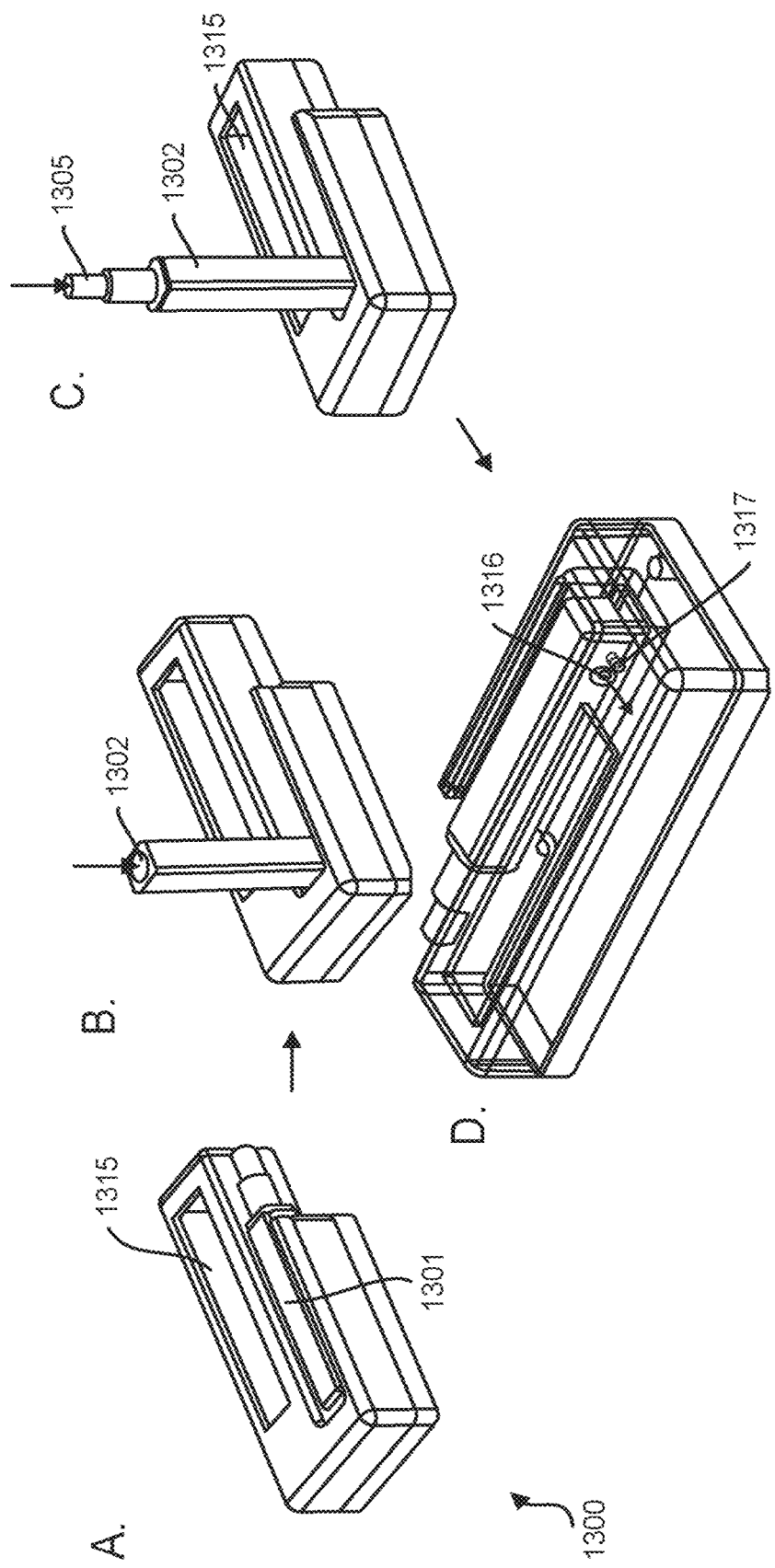
FIGS. 13A-D provide perspective and partial cross sectional views of devices according to embodiments of the disclosure.

One embodiment of a biological assay sample preparation device for use in practicing the subject methods is provided in FIGS. 13A-D. FIG. 13A shows the device in a stored configuration and FIG. 13B shows the device in a configuration such that a sample collector can be inserted therein. The device 1300 includes a sample receiving module 1301 including a fluid container 1302 for receiving one or more portions of a sample collector therein, e.g., entirely therein. Such a device 1300 can also include a cap 1305 operatively, e.g., removably, coupleable to the sample receiving module 1301 to pressurize the sample receiving module 1301, as is shown in FIG. 13C. The sample receiving module 1301, cap 1305 and other provided components can have any of the characteristics or combination of characteristics of sample receiving modules, caps and/or other corresponding components described herein.

In the embodiment shown, operatively coupling the sample receiving module 1301 and the cap 1305, as is shown in FIG. 13C, can expose a preparation solution to a sample on a sample collector and thereby produces a prepared, e.g., lysed, sample. Once the prepared, e.g., lysed, sample is made, the sample receiving module 1301 can be operatively coupled, fluidically coupled, such as by actuating, such as by rotating the sample receiving module 1301 about an axis of a coupling component 1317, via a vent 1316, to a preparation module 1315 of the device 1300. Operatively coupling can be performed by rotating the sample receiving module 1301 about an axis of a coupling component 1317 90° or less.

The preparation module 1315 also can include a buffer, e.g., a dilution buffer. Operatively coupling the sample receiving module 1301 and the preparation module 1315, as is shown in FIG. 13D, places the prepared sample in fluidic communication with the dilution buffer so that the prepared sample is diluted in the preparation module 1315. Thereafter, the diluted prepared sample can be delivered out of the device 1300 for further analysis using the pressure within the device to push the diluted prepared sample out of the device 1300.

Figure 14:
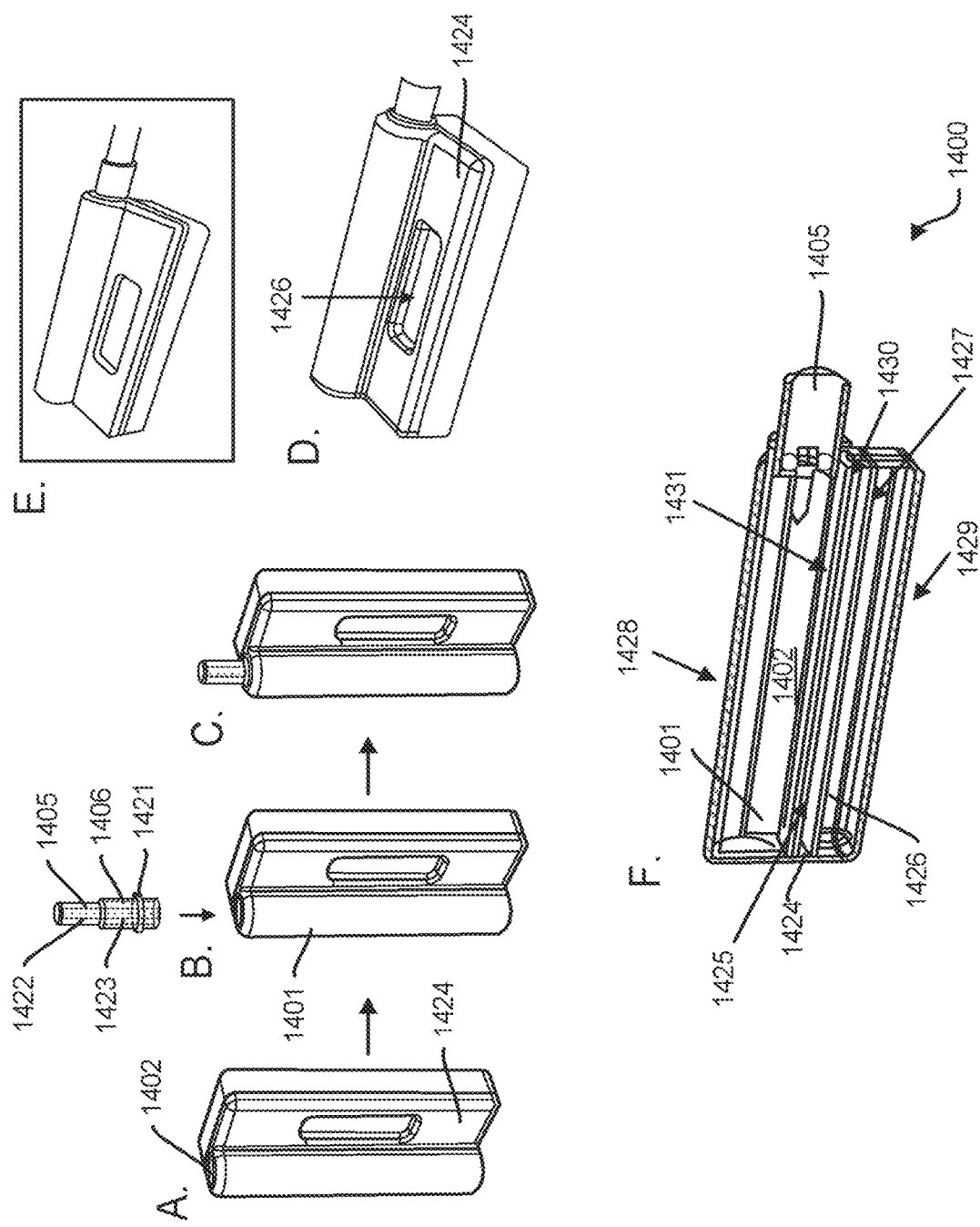
FIGS. 14A-F provide perspective views of devices according to various embodiments of the subject disclosure.

One version of a biological assay sample preparation device for use in practicing the subject methods is provided in FIGS. 14A-F. FIG. 14A shows the device in a configuration such that a sample collector can be inserted therein, as indicated by the arrow. The device 1400 includes a sample receiving module 1401 including a fluid container 1402 for receiving one or more portions of a sample collector therein, e.g., entirely therein. Such a device 1400 can also include a cap 1405 operatively, e.g., removably, coupleable to the sample receiving module 1401, as is shown in FIG. 14C. Such a cap 1405 can also include a preparation solution, e.g., a lysis buffer 1406, a seal 1421, and a plunger 1422 including a piercing member 1423. The plunger 1422 can be actuated by pushing the plunger 1422 to pierce the seal 1421 with the piercing member 1423, provide fluidic communication between the lysis buffer 1406 and a sample collector in the sample receiving module 1401, and pressurize the sample receiving module 1401. The sample receiving module 1401, cap 1405 and other provided components can have any of the characteristics or combination of characteristics of sample receiving modules, caps and/or other corresponding components described herein.

Once the prepared, e.g., lysed, sample is made, the prepared sample can pass to a sample incubation chamber 1424 via an actuating valve 1425 which can include a bimetal valve actuator. Therein, the sample can be incubated and the incubated sample measured to produce an assay result. The assay result can be displayed to a user via a display 1426 of the device 1400. The device 1400 also includes a power source 1426, e.g., one or more batteries, and a substrate 1427, e.g., a printed circuit board, for performing the measurement and displaying the result. The device 1400 also includes a housing composed of a top cover 1428 and a bottom cover 1429 and a bottom plate 1430 and/or gasket 1431 separating the sample receiving module 1401 and the incubation chamber 1424.

Methods

The present disclosure includes methods of delivering a sample, such as a biological assay sample. Delivering a sample can include moving, e.g., flowing, a sample, such as a prepared biological assay sample, to a particular location, such as a location outside a sample delivery device and/or a specific location intended by a user, such as a sample analysis device or a portion thereof.

In some aspects, the subject methods include collecting a biological sample with a sample collector. Such a sample can include, for example, human saliva, blood, or a solid tissue such as buccal tissue. Such a sample can also include bacteria or spores. Collecting can include contacting, e.g., rubbing and/or scraping, the sample collector against one or more surfaces of a subject and/or surfaces of a biological sample of a subject, such as a liquid, e.g., saliva and/or blood, sample extracted from the subject. As such, in some versions, collecting includes extracting one or more biological samples from the subject. In some versions, collecting the biological sample can include instructing a subject to produce a biological sample, such as by spitting onto and/or into a sample collector. Collecting the biological sample can also include retaining a biological sample or a portion thereof, e.g., one or more cells, on the sample collector while, for example transferring the sample collector to an assay device. In some instances, a sample collector is a swab and collecting the biological sample includes swabbing the inside of a subject's mouth to obtain the biological sample on the collector.

In some aspects, the methods include inserting a sample collector into a sample receiving module of a sample preparation device. Inserting can include moving one or more portions of the sample collector, e.g., the sample collection portion and/or the handle, into, such as fully into, a sample receiving module via an opening in the module. The inserting can include rubbing one or more portions of the sample collector against an interior wall of the sample receiving module. In some versions, the methods include retaining the one or more portions of the sample collector, e.g., the sample collection portion and/or the handle, within, such as fully within, the sample receiving module after insertion. In some embodiments, the methods include removing the one or more portions of the sample collector, e.g., the sample collection portion and/or the handle, from the sample receiving module after insertion. Also, in some aspects, a sample receiving module includes a seal, e.g., a breakable and/or frangible seal, such as a foil seal, over an opening and wherein inserting the sample collector into a sample receiving module of a sample preparation device includes breaking the seal, such as breaking the seal by exerting force on it with the sample collector, and inserting at least a portion of the sample collector through the opening.

The subject embodiments, in some versions also include inserting the sample collector by exposing the biological sample to a preparation solution within the sample receiving module to produce a prepared biological assay sample. Such exposure can include immersing the biological sample and/or sample collector entirely within the preparation solution. Also, producing the prepared biological sample can include exposing the preparation solution to one or more aspects of the biological sample, wherein such exposure results in a change in the biological sample, e.g., cell lysing, such that the modified biological sample can be further processed and/or analyzed.

A prepared biological assay sample is a biological assay sample which has been processed by exposing the sample to a preparation solution, as described above. Such exposure can prepare the sample for further analysis and can include lysing cells of the sample with a lysing agent of the preparation solution and/or extracting nucleic acids therefrom. Such extracted nucleic acids can be released into a resulting prepared sample solution. In some embodiments, the methods include a step of extracting genomic deoxyribonucleic acid (DNA) from a biological sample. In some versions, the preparation solution is a nucleic acid amplification preparation solution and exposure to the solution prepares nucleic acids of the sample for amplification, e.g., isothermal amplification. After such exposure, the sample is a prepared nucleic acid amplification sample.

In various aspects, the subject methods include operatively coupling a cap of the sample preparation device to the sample receiving module and thereby pressurizing the sample receiving module. Operatively coupling the cap of the sample preparation device to the sample receiving module can include adhesively, snapedly, and/or screwably, fastening the cap to the sample receiving module. Such coupling can also be removable and as such, reversible and repeatable a plurality of times. Such operative coupling can also in include sealing the sample receiving module or apportion thereof, e.g., a fluid container, with the cap. Operatively coupling the cap and the sample receiving module can include screwing the cap to the module by rotating the cap with respect to the module while screwable threads of the two elements are engaged. Operatively coupling the cap and the sample receiving module, in some embodiments includes inserting the sample receiving module or a portion thereof, e.g., an end, into a cap. Operatively coupling the cap and the sample receiving module, in some embodiments includes inserting the cap, or a portion thereof, e.g., a pressurizing component and/or an end, into, such as fully into, the sample receiving module or a portion thereof, e.g., a fluid container.

In some versions of the methods, the sample receiving module includes a first attachment element and/or the cap includes a second attachment element. In such embodiments, operatively coupling a cap of the sample preparation device to the sample receiving module includes mateably connecting the first and second attachment elements, such as screwing the first attachment element, e.g., a thread, into the second attachment element, e.g., a groove, by rotating the cap with respect to the sample receiving module while the attachment elements are engaged.

Operatively coupling the cap of the sample preparation device to the sample receiving module also includes pressurizing the sample receiving module or a portion thereof, e.g., a fluid container. The pressurizing includes exerting force on one or more fluid, e.g., a liquid and/or gas, within the sample receiving module, such as air and/or preparation solution with a pressurizing component. As the pressurizing component extends further into the sample receiving module, the pressure increases because the pressurizing component exerts more force on the one or more fluid. The methods also include retaining the pressurizing component in a particular position within the sample receiving module, wherein, in such a configuration, the pressure in the module remains constant while the sample receiving module remains sealed.

In various embodiments, the methods include pressurizing the sample receiving module to a pressure ranging from 50 Pa to 50,000 Pa, such as 500 Pa to 50,000 Pa, such as 1,000 Pa to 50,000 Pa, such as 5,000 Pa to 50,000 Pa, such as 10,000 Pa to 30,000 Pa, such as 15,000 Pa to 25,000 Pa, each inclusive. Where desired, the pressurizing component pressurizes the sample receiving module to a pressure of 1,000,000 Pa or less, such as 50,000 Pa or less, such as 30,000 Pa or less, such as 10,000 Pa or less, such as 5,000 Pa or less, such as 1,000 Pa or less, such as 500 Pa or less, such as 50 Pa or less. In some versions, the pressurizing component pressurizes the sample receiving module to a pressure of 1,000,000 Pa or more, 50,000 Pa or more, 30,000 Pa or more, 10,000 Pa or more, or 5,000 Pa or more, 1,000 Pa or more, 500 Pa or more, or 50 Pa or more. As used herein, the term pressure can refer to peak pressure.

Figure 16:
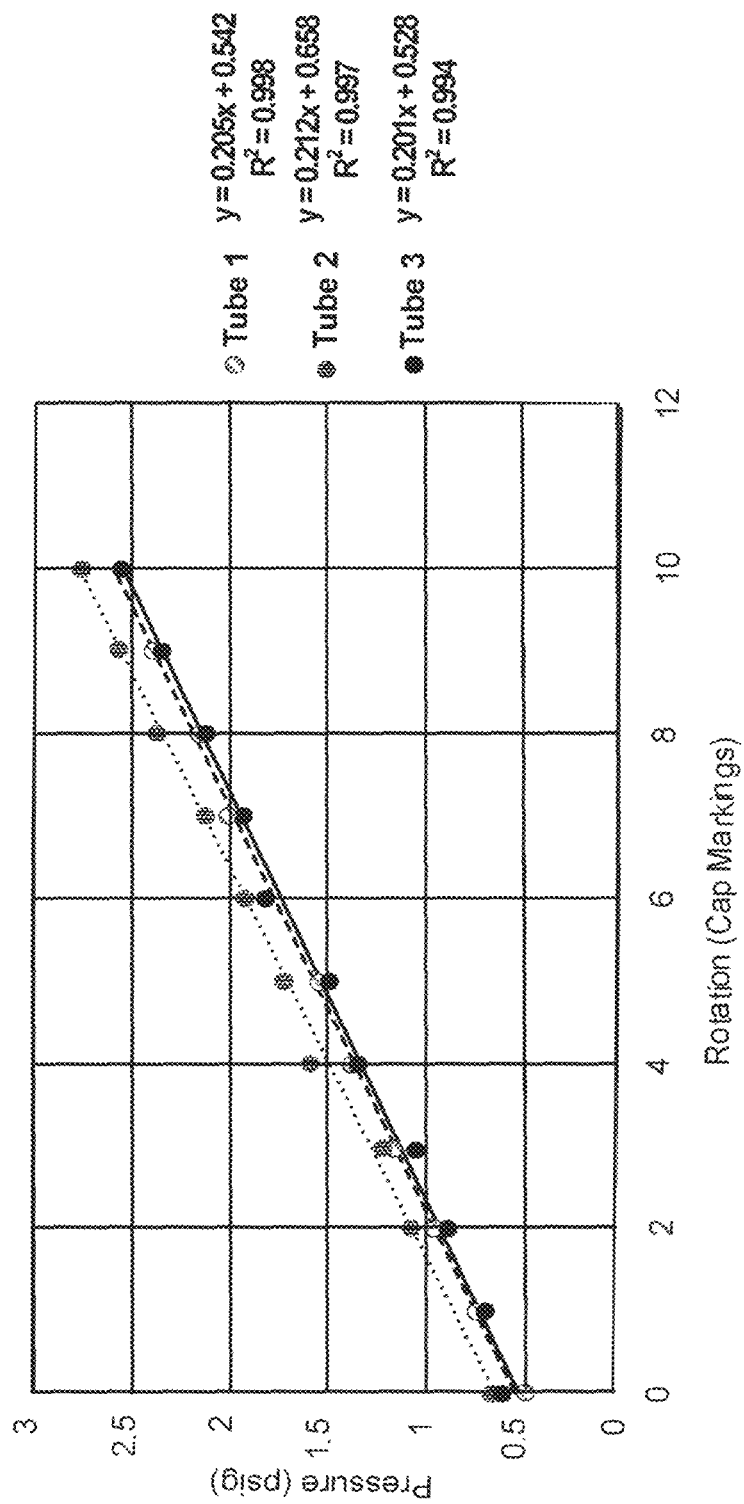
FIG. 16 provides pressure generated in a sample preparation device upon pressurization by the application and rotation of a cap, e.g., screw cap, to the top of the device according to embodiments of the subject disclosure.

One example of pressurization according to the subject embodiments is illustrated in FIG. 16. Specifically, FIG. 16 provides a graph illustrating pressure generated in a sample preparation device upon pressurization by the application and rotation of a cap, e.g., screw cap, to the top of the device according to embodiments of the subject disclosure. As is shown, pressure is linearly related to displacement, and therefore rotation, of the cap.

In some aspects, the methods include storing reagents with long shelf-life at room temperature. Such storage can include storing stable reagents, e.g., preparation solutions and/or staging reagents, in liquid form and/or unstable reagents, e.g., preparation solutions and/or staging reagents, in dry, e.g., lyophilized, form. Storage according to the subject methods can be performed for a length of time of 1 day or less, such as 1 month or less, such as 6 months or less, such as 1 year or less and/or one year or more. The methods also can include sample loading into, for example a sample analyzing device.

In various aspects, a solution, e.g., a lysis solution, is heated. Such heating can be achieved using a heat source such as an exothermic reaction. Furthermore, in some embodiments, the methods include adding to contents of a sample receiving module one or more heating reagents which, when mixed, cause an exothermal reaction. Such a reaction can, for example, heat a sample for lysis. Exothermal reactions can generate heat and/or gas. Exothermal reactions can include the hydration of a mixture composed of encapsulated and/or non-encapsulated oxides such as calcium oxide and/or magnesium oxide and dehydrated and/or hydrated zeolite, or any combinations thereof. Such a process can be coupled with control of pH of the mixture through compounds such as Citric acid, or combination exothermic mixes, such as Cao and Mg—Fe. Modulation can include timed/controlled release from encapsulated reactants and can include particles with tailored size distribution and different burn characteristics. Phase change materials (PCM) can be used to control the heat stability of the reaction. PCMs include, for example, organics (paraffins, non paraffins and fatty acids) and inorganics (salt hydrates).

Also, in some versions, the methods include adding one or more gas-producing regents, e.g., liquid reagents, that, when mixed, generate a gas and further pressurize a subject device or a portion thereof, e.g., a sample receiving module. Such reagents may be the same or different reagents than those applied in an exothermic reaction. The gas produced by such reagents may be applied in propelling at least a portion of the prepared biological assay sample out of the sample receiving module. In some forms, a chemical reaction is used to produce gases that can increase pressure, e.g., pressure which can be applied for driving out a liquid, inside the module.

The methods, in some instances, include generating fluid driving pressure and/or dispensing a prepared sample and/or reagent and sample mix into an analyzing device with the pressure. Also, according to various embodiments, a user can pressurize a sample receiving module on-demand before, during and/or after reagents, e.g., preparation solutions and/or staging reagents, are exposed to a biological sample.

One embodiment of the subject methods is illustrated, for example, by FIG. 1 and FIG. 15. In various embodiments, a device according to the methods includes a sample receiving module 101 including a fluid container 102 for receiving one or more portions of a sample collector therein, e.g., entirely therein, a preparation solution 104, and a first attachment element 103. Such a device 100 can also include a cap 105 operatively, e.g., removably, coupleable to the sample receiving module 101 and including a pressurizing component 106, and a second attachment element 107 operatively coupleable with the first attachment element 103. As noted above, the methods include operatively coupling the cap 105 and the sample receiving module 101. Such a process can be performed by causing a device to go from a conformation as shown in FIG. 1 or FIG. 2 to a conformation as shown in FIG. 15. Accordingly, the methods can include inserting a pressurizing component 106 into, e.g., entirely into, the sample receiving module 101. The methods can also include expelling fluid from sample receiving module 101 when the first attachment element 103 is operatively coupled to the second attachment element 107 by, for example, actuating a valve 108 of the device.

Furthermore, and as is illustrated, for example, by FIG. 2, the methods include actuating an inner body 214 within an outer body 209 when a cap 205 is operatively coupled to a sample receiving module 201. Operatively coupling the cap includes exerting force on the inner body 214 with the cap 205 or a portion thereof, such as a pressurizing component 206, so that the inner body 214 moves. Such actuating can also include breaking a breakable seal 213 with the one or more piercing member 216 and placing the first chamber 210 in fluidic communication with the second chamber 215. Also, in some versions, the outer body 209 includes a staging reagent 217 and the methods include placing the staging reagent 217 in fluidic communication with the second chamber 215. In some aspects, the staging reagent 217 includes one or more lyophilized agents, such as one or more lyophilized cell lysing reagent, and placing the staging reagent 217 in fluidic communication includes hydrating the reagent with the preparation solution 204 and/or exposing the staging reagent 217 to the biological sample.

Embodiments of the subject methods also include delivering a sample, e.g., a prepared biological assay sample, by depressurizing the sample receiving module by flowing and/or discharging at least a portion of the contents of the sample receiving module, such as a prepared biological assay sample, preparation solution, unprepared biological sample and/or air, out of the sample receiving module. Depressurizing includes providing fluidic communication, such as via a valve, e.g., a reversibly actuable valve, between a fluidic container of a sample receiving module and an environment, such as a sample analysis device, outside the sample receiving module. Such depressurization can include actuating the valve from a sealed conformation to an unsealed conformation and thereby providing such fluidic communication via an opening, e.g., a depressurization opening, therethrough. In various embodiments, an opening such as a depressurization opening does not allow passage of a gas, such as air, therethrough. In such embodiments, air is not passed through the opening while, for example, a liquid is passed through the opening, the plunger actuates toward the opening and/or the plunger is not actuated.

Where desired, a device according to the subject embodiments includes a breakable and/or frangible seal, such as a foil seal, for sealing a valve, e.g., a reversibly actuable valve. In such embodiments, depressurizing the sample receiving module includes breaking the seal so that a fluid can flow from a first side of the seal to a second side of the seal opposite the first. Breaking the seal can include exerting force on it with fluid within the pressurized container by opening the valve. Also, in some versions, the subject devices can include a filter for filtering fluid discharging from the sample receiving module. In such embodiments, the methods include filtering by flowing one or more fluid, e.g., a prepared biological assay sample and/or air, through the filter. Flowing can be achieved by passing the fluid through the material of the filter, such as through one or more entire surface, e.g., a top and/or bottom surface of the material. The filtering can be performed on the fluid, e.g., sample, discharging from a depressurizing sample receiving module through, for example, a valve.

In some aspects of the methods, the sample receiving module includes an outer body forming a first chamber, and a fluid container of a sample receiving module includes a breakable seal and an inner body forming a second chamber which can be sealed at an end by the breakable seal, wherein the inner body is actuable within the outer body. In such embodiments, operatively coupling a cap of the sample preparation device to the sample receiving module includes actuating, such as by sliding, the inner body within the outer body to break the seal and place the first and second chambers in fluidic communication. Operatively coupling, such as by screwing, a cap of the sample preparation device to the sample receiving module can include exerting force on the inner body with the cap or a portion thereof, e.g., the pressurizing component, by contacting the two components. Actuating the inner body within the outer body includes moving the inner body in a linear direction toward a valve of the sample receiving module and/or away from the cap. In some versions, the outer body includes a piercing member and actuating the body includes piercing the seal on the inner body with the piercing member. Also, in various aspects, an outer body includes a staging reagent, e.g., a lyophilized staging reagent, and placing the first and second chambers in fluidic communication includes mixing the preparation solution and/or biological sample and the staging reagent and/or hydrating the staging reagent.

Also included in the subject methods are methods for preparing a biological assay sample including operatively coupling a cap and a sample receiving module of a biological assay sample preparation device, wherein the cap includes a seal and a plunger including a piercing member, e.g., a needle and/or sharpened cylindrical protrusion. In such methods, operatively coupling can include inserting, e.g., fully inserting, a portion of a cap, e.g., an insertion portion and/or an end, into a sample receiving module or a portion, e.g., chamber thereof. Such insertion can form a sealed fluidic connection between chambers of each element. Also, an insertion portion can be cylindrical and can extend at and end from and have a smaller diameter than other portions of the cap. An insertion portion can be at a first end of a cap opposite a second end, wherein the second end includes a plunger.

The methods also, in some aspects include advancing the plunger to pierce the seal with the piercing member and thereby placing a first chamber in fluidic communication with a second chamber and preparing a biological assay sample. Such advancing can include moving, such as by sliding, the plunger in a linear direction, such as a direction toward a sample receiving module or a portion thereof, e.g., a valve, and/or a direction along an axis of symmetry of the plunger and/or the cap and/or the sample receiving module. The plunger can include a first end and a second end opposite the first end and including the piercing member, and wherein advancing the plunger includes exerting force on a first end of the plunger in a direction toward the second end. Advancing the plunger can be performed manually by, for example, contacting and exerting force directly on an end of the plunger, as can be performed with the device embodiment shown for example, in FIGS. 3A and 3B and 4. Advancing the plunger can also be performed by, screwing the cap to the sample receiving module, such as by twisting the two components with respect to one another while their respective attachment elements are engaged, as can be performed with the device embodiment shown for example, in FIGS. 5A and 5B.

Also, in some versions, the plunger includes a body portion, e.g., a cylindrical body portion, which is received entirely within other portions of the cap when the plunger is advanced, and a contacting portion at an end of the body portion and which can be contacted by a user directly to advance the plunger. Also, as is sown, for example in FIGS. 5A and 5B, in some versions, the plunger is retained entirely within other portions of the cap while it is advanced.

In various embodiments of the subject disclosure, a first chamber, e.g., first chamber of a cap, includes a preparation solution, and a second chamber, e.g., second chamber of a sample receiving module, includes a staging reagent. In such embodiments, the methods can include placing the first chamber in fluidic communication with the second chamber and mixing the preparation solution and the staging reagent. Also, in some embodiments of the methods, delivering the prepared biological assay sample includes actuating, such as by rotating 45° or less, or 90° or less, a reversibly actuable valve of the sample preparation device and flowing at least a portion of the prepared biological assay out of the sample receiving module through the valve, e.g., through an opening in the valve.

Furthermore, and as is representatively shown, for example, by FIGS. 6A-C, the methods include using a device 600 composed of a sample receiving module 601 including a fluid container 602 for receiving one or more portions of a sample collector 611 therein, e.g., entirely therein, and a first attachment element 603. The methods include operatively coupling a cap 605 and the sample receiving module 601, as is shown in FIG. 6B. The sample receiving module 601 in turn includes a preparation solution, e.g., a lysis buffer 606, and a second attachment element 607 operatively coupleable with the first attachment element 603 when the components are operatively coupled.

In some versions, the methods include operatively coupling the sample receiving module 601 and the cap 605, by screwing the sample receiving module 601 and the cap 605, and thereby piercing a seal 604 with a piercing member 608 and placing a first chamber 609 in fluidic communication with a second chamber 610. As such, operatively coupling the sample receiving module 601 and the cap 605, such as by screwing the sample receiving module 601 and the cap 605 together, includes exposing a preparation solution 606 to a sample on a sample collector 611 and thereby producing a prepared, e.g., lysed, sample 612.

Once the prepared, e.g., lysed, sample 612 is made, the methods include operatively coupling the sample receiving module 601 to a pressurizing module 615. Operatively coupling can be performed by attaching, such as by screwing, an attachment element 613 of a sample receiving module 601 and a second attachment element 614 of a pressurizing module 615. The pressurizing module 615 also includes a buffer, e.g., a dilution buffer 616. Operatively coupling the sample receiving module 601 and the pressurizing module 615, as is shown in FIG. 6C, can include placing the prepared sample 612 in fluidic communication with the dilution buffer 616 so that the prepared sample 612 is diluted and pressurizes the sample receiving module. Such an action can also pierce a seal 617 with a piercing member 618. Thereafter, the methods can include delivering the diluted prepared sample out of the device 600 for further analysis using the pressure within the device to push the diluted prepared sample out of the device 600.

As is representatively shown, for example, by FIGS. 7A-D, the methods include using a device 700 including a sample receiving module 701 including a fluid container 702 for receiving one or more portions of a sample collector 711 therein, e.g., entirely therein, and a first attachment element 703. Such a device 700 can also include a cap 705 and the methods can include operatively coupling the cap 705 to the sample receiving module 701. The cap 705 also can include a preparation solution, e.g., a lysis buffer 706, and a second attachment element 707 operatively coupleable with the first attachment element 703. Operatively coupling the cap 705 and the sample receiving module 701 also includes pressurizing the sample receiving module 701. The sample receiving module 701 can also include a buffer, e.g., a dilution buffer 718 in a buffer container 719 therein.

In the embodiment shown, operatively coupling the sample receiving module 701 and the cap 705, as is shown in FIG. 7B, such as by screwing the sample receiving module 701 and the cap 705, includes piercing a seal 704 with a piercing member 708 and placing a first chamber 709 in fluidic communication with a second chamber 710. As such, operatively coupling the sample receiving module 701 and the cap 705, such as by screwing the sample receiving module 701 and the cap 705 together, includes exposing preparation solution 706 to a sample on a sample collector 711 and thereby producing a prepared, e.g., lysed, sample 712.

After the prepared, e.g., lysed, sample 712 is made, the methods include operatively coupling the sample receiving module 701 to, such as by lowering onto, a cartridge 715. Such operative coupling can include actuating a fluidic communication element 717 and/or opening a valve 716, e.g., poppet valve, of the fluidic communication element 717. The methods also include actuating the fluidic communication element 717 toward the cap 705 by exerting force on it with the cartridge 715. Opening the valve 716 in turn includes releasing the prepared sample 712 into the dilution buffer 718 in the buffer container 719 and producing a prepared diluted sample 720. Operatively coupling the sample receiving module 701 and the cartridge 715, as is shown in FIG. 7D, includes delivering the prepared diluted sample 720 out of the sample receiving module 703 and into the cartridge.

In addition, and as is illustrated representatively, for example, by FIGS. 8A-D, the methods include using a device 800 including a sample receiving module 801 including a fluid container 802 for receiving one or more portions of a sample collector 811 therein, e.g., entirely therein. Such a device 800 can also include a cap 805 and the methods can include operatively coupling the cap 805 to the sample receiving module 801. The cap can also include a preparation solution, e.g., a lysis buffer 806.

Operatively coupling the cap 805 and the sample receiving module 801 may not pressurize the sample receiving module 801 but may include placing the lysis buffer 806 in fluidic communication with a sample on the sample collector 811 and thereby producing a prepared, e.g., lysed, sample 812.

The device 800 also includes a pressurizing chamber 816 operatively coupled to the sample receiving module 801 and including a valve 817, e.g., a one-way valve, to provide fluidic communication therebetween. The methods include actuating a plunger 818 to create positive and/or negative pressure within a pressurization chamber 816. The pressurizing chamber 816 also includes a buffer, e.g., a dilution buffer 821. The pressurizing chamber 816 also includes an expulsion valve 819 and the methods include expelling a diluted prepared sample 820 therefrom by actuating the plunger 818.

According to the subject methods, when the cap 805 is operatively coupled to the sample receiving module 801 to produce a prepared sample 812, the methods include actuating the plunger 818 in a first direction, as is shown in FIG. 8C, and propelling the prepared sample 812 from the sample receiving module 801 into the pressurizing chamber 816 via valve 817 and thereby producing a diluted prepared sample 820. The plunger 818 can then be actuated in a second direction opposite the first, as is shown in FIG. 8D, to thereby propel the diluted prepared sample 820 out of the pressurizing chamber 816 via expulsion valve 819.

As is shown representatively, for example, by FIGS. 8A-D, the methods include using a device 900 which includes a sample receiving module 901 including a fluid container 902 for receiving one or more portions of a sample collector 911 therein, e.g., entirely therein. Such a device 900 can also include a cap 905 operatively, e.g., removably, coupleable to the sample receiving module 901 and including a preparation solution, e.g., a lysis buffer 906. As such, the methods can include operatively coupling the cap 905 and the sample receiving module 901.

Operatively coupling the cap 905 and the sample receiving module 901 may not pressurize the sample receiving module 901 but may place the lysis buffer 906 in fluidic communication with a sample on the sample collector 911 and thereby produce a prepared, e.g., lysed, sample 912. The sample receiving module 901, cap 905 and other provided components can have any of the characteristics or combination of characteristics of sample receiving modules, caps and/or other corresponding components described herein.

In various instances, the device 900 also includes a pressurizing chamber 916 and the methods include operatively coupling the pressurizing chamber 916 to the sample receiving module 901. The pressurizing chamber 916 also includes a plunger 918, e.g., a manually actuable plunger, which and the methods include actuating the plunger to create positive and/or negative pressure within the pressurizing chamber 916.

The device 900 is configured such that when the cap 905 is operatively coupled to the sample receiving module 901 to produce a prepared sample 912, the plunger 918 can be actuated in a first direction according to the subject methods, as is shown in FIG. 9C, to propel the prepared sample 912 from the sample receiving module 901 and into the pressurizing chamber 916 via vent 917 and thereby produce a diluted prepared sample 920. Actuating the plunger 918 in such as direction can include unsealing a vent 917. The methods also include actuating the plunger 918 in a second direction opposite the first, as is shown in FIG. 9D, and propelling the diluted prepared sample 920 out of the pressurizing chamber 916 via the valve 919. Actuating the plunger 918 in such as direction can include sealing the vent 917 and preventing further fluid communication therethrough.

As is shown representatively, for example, by FIGS. 10, 11 and 12, the methods include using a device, e.g., device 1000, 1100, and/or 1200, which includes a sample receiving module 1001 including a fluid container 1002 for receiving one or more portions of a sample collector 1011 therein, e.g., entirely therein. As such, the methods include inserting such a sample collector therein. Such a device 1,000 can also include a cap 1005 operatively, e.g., removably, coupleable to the sample receiving module 1001 and the methods include operatively coupling the cap 1005 and the sample receiving module 1001. In some versions, operatively coupling the cap 1005 and the sample receiving module 1001 includes placing a preparation solution, e.g., a lysis buffer, in fluidic communication with a sample on the sample collector 1011 and thereby producing a prepared, e.g., lysed, sample.

The pressurizing chamber 1016 also includes a plunger 1018, e.g., a manually actuable plunger, and the methods include pushing and/or pulling the plunger in a linear direction, e.g., along a central axis of symmetry of a pressurizing chamber and/or sample receiving module, and thereby creating positive and/or negative pressure within the pressurization chamber 1016 and/or sample receiving module 1001. The sample receiving module 1001 also includes an expulsion valve 1019 and the methods include expelling a diluted prepared sample therefrom upon actuation of the plunger 1018.

The methods include actuating the plunger 1018 in a first direction, to propel a buffer from channel 1017 into the sample receiving module 1001 and thereby produce a diluted prepared sample therein and pressurize the sample receiving module. According to the methods, the diluted prepared sample can then be propelled by the pressure out of the sample receiving module 1001 via expulsion valve 1019.

Also, in some versions of the methods, the methods include operatively coupling by screwing the cap 1005 to the sample receiving module 1001. The methods also can include screwing, such as by twisting, the plunger 1018 to actuate it into the pressurizing chamber 1016 to pressurize the pressurizing chamber 1016 and/or the sample receiving module 1001.

As is shown representatively, for example by FIGS. 13A-D, the methods include using a device 1300. Such methods can include storing the device 1300 in a stored configuration, such as that shown in FIG. 13A. The methods also can include inserting, such as fully inserting, a sample collector as indicated by the arrow into a device 1300 in a sample collector receiving configuration as shown in FIG. 13B. A device 1300 can also include a cap 1305 and the methods can include operatively, e.g., removably, coupling the cap 1305 to the sample receiving module 1301 and thereby pressurizing the sample receiving module 1301, as is shown in FIG. 13C.

Also, operatively coupling the sample receiving module 1301 and the cap 1305, as is shown in FIG. 13C, can include exposing a preparation solution to a sample on a sample collector and thereby producing a prepared, e.g., lysed, sample. Once the prepared, e.g., lysed, sample is made, the methods include operatively coupling, such as fluidically coupling, such as by actuating, such as by rotating, the sample receiving module 1301 about an axis of a coupling component 1317, wherein the operative coupling is via a vent 1316, to a preparation module 1315 of the device 1300.

Operatively coupling the sample receiving module 1301 and the preparation module 1315, as is shown in FIG. 13D, can include placing the prepared sample in fluidic communication with a dilution buffer so that the prepared sample is diluted in the preparation module 1315. Thereafter, the methods can include moving the diluted prepared sample out of the device 1300 for further analysis using the pressure within the device to push the diluted prepared sample out of the device 1300.

As is shown representatively, for example by FIGS. 14A-F, the methods include using a device 1400 including a sample receiving module 1401 including a fluid container 1402 for receiving one or more portions of a sample collector therein, e.g., entirely therein. Such a device 1400 can also include a cap 1405 and the methods include operatively, e.g., removably, coupling the cap 1405 to the sample receiving module 1401, as is shown in FIG. 14C. Such a cap 1405 can also include a preparation solution, e.g., a lysis buffer 1406, a seal 1421, and a plunger 1422 including a piercing member 1423. The methods include actuating the plunger 1422 by pushing the plunger 1422 to pierce the seal 1421 with the piercing member 1423, providing fluidic communication between the lysis buffer 1406 and a sample collector in the sample receiving module 1401, and pressurizing the sample receiving module 1401.

Once the prepared, e.g., lysed, sample is made, the methods include flowing the prepared sample to a sample incubation chamber 1424 via an actuating valve 1425 which can include a bimetal valve actuator. Therein, the sample can be incubated according to the subject methods and the incubated sample measured to produce an assay result. The assay result can be displayed to a user via a display 1426 of the device 1400. Furthermore, FIG. 14F provides a cross sectional view of the device.

Kits

The embodiments disclosed herein also include kits including the subject devices and which can be used according to the subject methods. The subject kits can include two or more, e.g., a plurality, three or less, four or less, five or less, ten or less, or fifteen or less, or fifteen or more, sample preparation devices or components thereof, according to any of the embodiments described herein, or any combinations thereof.

The kits can include one or more solutions and/or reagents, such as any of those described herein, e.g., preparation solutions and/or staging reagents and/or buffers, which can be stored in the kits in containers separate from the devices. In addition, the kits can include any device or other element which can facilitate the operation of any aspect of the kits. For example, a kit can include one or more devices for receiving and/or analyzing one or more characteristics of a sample, e.g., a prepared sample. Kits can also include packaging, e.g., packaging for shipping the devices without breaking.

In certain embodiments, the kits which are disclosed herein include instructions, such as instructions for using devices. The instructions for using devices are, in some aspects, recorded on a suitable recording medium. For example, the instructions can be printed on a substrate, such as paper or plastic, etc. As such, the instructions can be present in the kits as a package insert, in the labeling of the container of the kit or components thereof (i.e., associated with the packaging or subpackaging etc.). In other embodiments, the instructions are present as an electronic storage data file present on a suitable computer readable storage medium, e.g., Portable Flash drive, CD-ROM, diskette, etc. The instructions can take any form, including complete instructions for how to use the devices or as a website address with which instructions posted on the world wide web can be accessed.

Utility

As demonstrated above, the subject devices and methods are directed to biological sample preparation devices and methods for preparing and delivering biological assay samples. Reagent storage, release and/or other manipulation has been performed by storing reagents in vials that are opened manually by an operator and manipulated using pipettes to, for example, aliquot, mix and/or incubate the reagents. Attempts at resolving challenges associated with reagent storage and/or manipulation such as complexity, large time requirement, and inconvenience have included, for example, applying blister packs and dry reagent storage to utilizing fluidic networks driven by active pressure sources such syringe pumps, compressors, peristaltic pumps and pressurized canisters. Many of the attempts have included applying separate structures on a device and utilizing active components. Such previous attempts have involved a high degree of complexity and cost which in turn has provided limited reliability and usability.

The disclosed subject matter addresses these issues with the described user-powered integrated device that provides reagent storage/release and fluid propulsion. As such, the subject embodiments integrate and thus simplify steps including, for example, aliquoting, mixing, measuring and/or incubating using the described self-contained automatic fluidic device. Accordingly, the subject methods and devices are cheaper, less complex and/or more accurate than other such devices or methods. Thus, the subject devices and methods can be applied, for example, to provide efficient on-demand reagent storage and/or release by using effective fluid manipulation, including propulsion, of a sample and/or reagents.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

The invention claimed is:

1. A method of delivering a biological assay sample, the method comprising:
   a. collecting a biological sample with a sample collector;
   b. inserting the sample collector into a sample receiving module of a sample preparation device, wherein inserting the sample collector comprises exposing the biological sample to a preparation solution to produce a prepared biological assay sample, wherein the sample receiving module comprises an outer body forming a first chamber, an inner body forming a second chamber, and a first attachment element, wherein the outer body comprises a piercing member, and wherein the inner body comprises a breakable seal and is movable within the outer body;
   c. operatively coupling a cap of the sample preparation device to the sample receiving module and thereby pressurizing the prepared biological assay sample within the sample receiving module, wherein the cap comprises a second attachment element operatively coupleable with the first attachment element and wherein operatively coupling the cap comprises moving the inner body within the outer body to break the breakable seal and place the first and second chambers in fluidic communication; and
   d. depressurizing the prepared biological assay sample within the sample receiving module by flowing at least a portion of the prepared biological assay sample out of the sample receiving module.

2. The method according to claim 1, wherein the preparation solution comprises a nucleic acid preparation solution.

3. The method according to claim 1, wherein the preparation solution is a nucleic acid amplification preparation solution.

4. The method according to claim 3, wherein the prepared sample comprises a prepared nucleic acid amplification sample.

5. The method according to claim 1, wherein the prepared sample is a prepared nucleic acid amplification sample.

6. The method according to claim 1, wherein the cap comprises a pressurizing component and operatively coupling the cap comprises inserting the pressurizing component into the sample receiving module.

7. The method according to claim 1, wherein operatively coupling the cap of the sample preparation device to the sample receiving module comprises inserting an end of the sample receiving module into the cap.

8. The method according to claim 1, wherein operatively coupling the cap of the sample preparation device to the sample receiving module comprises screwing the sample receiving module to the cap.

9. The method according to claim 1, wherein pressurizing the sample receiving module comprises pressurizing the module to a peak pressure ranging from 10,000 Pa to 30,000 Pa.

10. The method according to claim 1, wherein the sample receiving module is shaped as a cylinder having a diameter of 5 cm or less and having a height of 20 cm or less.

11. The method according to claim 1, wherein the sample receiving module has a volume ranging from 1 $cm^3$ to 50 $cm^3$.

12. The method according to claim 1, wherein the cap is operatively coupled to a first end of the sample preparation device and an actuable valve is at a second end of the sample preparation device opposite the first end.

13. The method according to claim 1, wherein the device further comprises a filter and the method further comprises filtering a sample fluid with the filter prior to discharging sample fluid.

14. The method according to claim 1, wherein the outer body comprises a staging reagent and wherein placing the first and second chambers in fluidic communication comprises mixing the prepared biological assay sample and the staging reagent.

15. The method according to claim 1, wherein operatively coupling the cap of the sample preparation device to the sample receiving module comprises mateably connecting the first and second attachment elements.

16. The method according to claim 1, wherein the sample receiving module further comprises a second breakable seal over an opening and wherein inserting the sample collector into the sample receiving module of the sample preparation device comprises breaking the second breakable seal and inserting at least a portion of the sample collector through the opening.

17. The method according to claim 1, further comprising delivering one or more heating reagents into the sample receiving module which, when delivered, cause an exothermal reaction and heat the biological sample.

18. The method according to claim 1, further comprising delivering one or more gas-producing reagents into the sample receiving module which, when delivered, generate a gas.

19. The method according to claim 1, wherein the device further comprises a filter and the method comprises concentrating one or more particles of the biological sample by flowing at least a portion of the prepared biological assay sample through the filter.

20. The method according to claim 1, wherein the sample receiving module further comprises an actuable valve.

21. The method according to claim 20, wherein flowing at least a portion of the prepared biological assay sample out of the sample receiving module comprises flowing the prepared biological assay sample through the actuable valve.

22. The method of claim 14, wherein the staging reagent is a lyophilized lysing reagent.

* * * * *